United States Patent
Hubschwerlen et al.

(10) Patent No.: US 8,507,478 B2
(45) Date of Patent: Aug. 13, 2013

(54) OXAZOLIDINYL ANTIBIOTICS

(75) Inventors: Christian Hubschwerlen, Durmenach (FR); Georg Rueedi, Allschwil (CH); Jean-Philippe Surivet, Kembs (FR); Cornelia Zumbrunn-Acklin, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 101 days.

(21) Appl. No.: 13/123,708

(22) PCT Filed: Oct. 9, 2009

(86) PCT No.: PCT/IB2009/054433
§ 371 (c)(1), (2), (4) Date: Apr. 11, 2011

(87) PCT Pub. No.: WO2010/041218
PCT Pub. Date: Apr. 15, 2010

(65) Prior Publication Data
US 2011/0201595 A1 Aug. 18, 2011

(30) Foreign Application Priority Data
Oct. 10, 2008 (WO) .................. PCT/IB2008/054175

(51) Int. Cl.
- *A61K 31/5415* (2006.01)
- *A61K 31/538* (2006.01)
- *A61K 31/498* (2006.01)
- *A61K 31/4985* (2006.01)
- *A61K 31/4704* (2006.01)

(52) U.S. Cl.
USPC .................. 514/224.2; 514/230.8; 514/249; 514/312; 544/48; 544/52; 544/105; 544/350; 544/353; 546/157

(58) Field of Classification Search
USPC .............. 544/48, 52, 105, 350, 353; 546/157
See application file for complete search history.

(56) References Cited

U.S. PATENT DOCUMENTS
| | | |
|---|---|---|
| 2009/0198063 A1 | 8/2009 | Kiyoto et al. |
| 2010/0168418 A1 | 7/2010 | Kiyoto et al. |

FOREIGN PATENT DOCUMENTS
| | | |
|---|---|---|
| EP | 0518672 | 12/1992 |
| WO | WO 02/066470 | 8/2002 |
| WO | WO 2006/090272 | 8/2006 |
| WO | WO 2006/134378 | 12/2006 |
| WO | WO 2006/137485 | 12/2006 |
| WO | WO 2007/138974 | 12/2007 |
| WO | WO 2007/144423 | 12/2007 |
| WO | WO 2008/006648 | 1/2008 |
| WO | WO 2008/009700 | 1/2008 |
| WO | WO 2008/026172 | 3/2008 |
| WO | WO 2008/065198 | 6/2008 |
| WO | WO 2008/071961 | 6/2008 |
| WO | WO 2008/071964 | 6/2008 |
| WO | WO 2008/071981 | 6/2008 |
| WO | WO 2009/077989 | 6/2009 |
| WO | WO 2009/104159 | 8/2009 |

OTHER PUBLICATIONS

Cha, Jin Kun et al., "Acyclic Stereocontrol Induced by Allylic Alkoxy Groups. Synthetic Applications of Stereoselective Dihydroxylation in Natural Product Synthesis," Chemical Reviews, ACS Publications by the American Chemical Society, 1995, vol. 95, No. 6, pp. 1761-1795.

(Continued)

*Primary Examiner* — Brian McDowell
(74) *Attorney, Agent, or Firm* — Hunton & Williams LLP

(57) ABSTRACT

The invention relates to antibacterial compounds of formula I

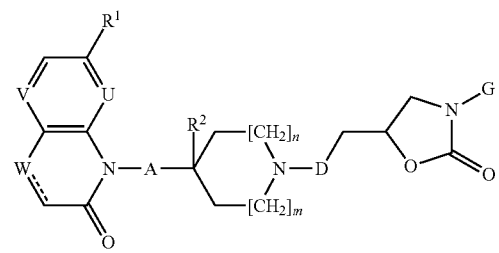

wherein $R^1$ is alkoxy or halogen; U and V each independently are CH or N; "-----" is a bond or is absent; W is CH or N or, when "-----" is absent, W is $CH_2$ or NH, with the proviso that U, V and W are not all N; A is a bond or $CH_2$; $R^2$ is H or, provided A is $CH_2$, may also be OH; m and n each independently are 0 or 1; D is $CH_2$ or a bond; G represents a phenyl group substituted once or twice in the meta and/or para position(s) by substituents selected from alkyl, ($C_1$-$C_3$)alkoxy and halogen, or G is a group $G^1$ or $G^2$

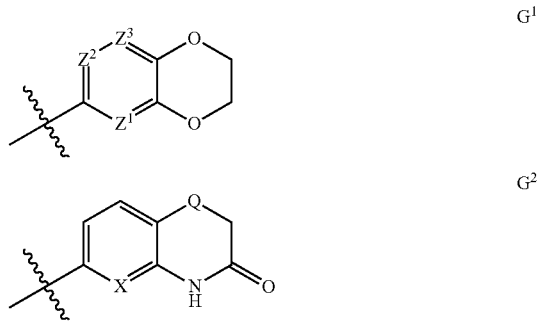

wherein $Z^1$, $Z^2$ and $Z^3$ may each represent CH or N; X is N or CH and Q is O or S; it being understood that if m and n each are 0, then A is $CH_2$;
and salts of such compounds.

17 Claims, No Drawings

(56) References Cited

OTHER PUBLICATIONS

Kolb, Hartmuth et al., "Catalytic Asymmetric Didroxylation," Chemical Reviews, ACS Publications by the American Chemical Society, 1994, vol. 94, No. 8, pp. 2483-2547.

Talbot, George et al., "Bad Bugs Need Drugs: An Update on the Development Pipeline from the Antimicrobial Availability Task Force of the Infectious Diseases Society of America," Clinical Infectious Diseases by the Infectious Diseases Society of America, 2006, vol. 42, pp. 657-658.

"Comprehensive Organic Transformations, A Guide to Functional Group Preparations," 2nd Edition, vol. 2, pp. 779-784, 1999.

"Comprehensive Organic Transformations, A Guide to Functional Group Preparations," 2nd Edition, vol. 2, pp. 821-828, 1999.

Mancuso, Anthony et al., "Oxidation of long-chain and related alcohols to carbonyls by dimethyl sulfoxide 'activated' by oxalyl chloride," The Journal of Organic Chemistry, vol. 43, No. 12, pp. 2480-2482, 1978.

Dess, D.B. et al., "Readily accessible 12-I-5 oxidant for the conversion of primary and secondary alcohols to aldehydes and ketones," The Journal of Organic Chemistry, vol. 48, No. 22, pp. 4155-4156, 1983.

Gould, Philip, "Salt selection for basic drugs," International Journal of Pharmaceuticals, vol. 33, pp. 201-217, 1986.

Sternfeld, Francine et al., "Synthesis and Serotonergic Activity of 3-[2-(Pyrrolidin-1-yl)ethyl]indoles: Potent Agonists for the h5-$HT_{1D}$ Receptor with High Selectivity over the h5-$HT_{1B}$ Receptor," Journal of Medical Chemistry by the American Chemical Society, vol. 42, pp. 677-690, 1999.

Greene, Theodora, "Protection for the Hydroxyl Group, Including 1,2- and 1,3-Diols," P.G.M. Wuts, Protecting Groups in Organic Synthesis, $3^{rd}$ Edition, pp. 133-139 and 142-143, 1999.

Greene, Theodora, "Protection for the Hydroxyl Group, Including 1,2- and 1,3-Diols," P.G.M. Wuts, Protecting Groups in Organic Synthesis, $3^{rd}$ Edition, pp. 494-653, 1999.

Greene, Theodora, "Protection for the Hydroxyl Group, Including 1,2- and 1,3-Diols," P.G.M. Wuts, Protecting Groups in Organic Synthesis, $3^{rd}$ Edition, pp. 23-147, 1999.

Greene, Theodora, P.G.M. Wuts, Protecting Groups in Organic Synthesis, Wiley-Interscience, 1999.

Chen, Yao-Jung, et al., 1,1,1-Tris(hydroxymethyl)ethane as a New, Efficient, and Versatile Tripod Ligand for Copper-Catalyzed Cross-Coupling Reactions of Aryl Iodides with Amides, Thiols, and Phenols, Organic Letters from the Department of Chemistry, National Chung-Hsing University, Taichung Taiwan, vol. 8, No. 24, pp. 5609-5612, 2006.

"Remington: The Science and Practice of Pharmacy," $21^{st}$ Edition, Lippincott, Williams and Wilkins Publishing, The University of the Sciences in Philadelphia, 2005.

OXAZOLIDINYL ANTIBIOTICS

CROSS-REFERENCE TO RELATED APPLICATIONS

This application is the national phase application of PCT/IB2009/054433, filed Oct. 9, 2009, which claims the benefit of PCT/IB2008/054175, filed Oct. 10, 2008, the contents of each are hereby incorporated by reference in their entirety.

FIELD OF THE INVENTION

The present invention concerns novel oxazolidinyl antibiotic compounds, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

BRIEF SUMMARY OF THE INVENTION

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:
  *S. aureus* is resistant to β-lactams, quinolones and now even to vancomycin;
  *S. pneumoniae* is becoming resistant to penicillin or quinolone antibiotics and even to new macrolides;
  *Enteroccocci* are quinolone and vancomycin resistant and β-lactam antibiotics are inefficacious against these strains;
  *Enterobacteriacea* are cephalosporin and quinolone resistant;
  *P. aeruginosa* are β-lactam and quinolone resistant.

Furthermore, the incidence of multi-drug-resistant Gram-negative strains such as *Enterobacteriacae* and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome multidrug-resistant Gram-negative bacilli such as *A. baumannii*, ESBL-producing *E. coli* and *Klebsiella* species and *Pseudomonas aeruginosa* (*Clinical Infectious Diseases* (2006), 42, 657-68).

In addition, microorganisms that are causing persistent infections are increasingly being recognized as causative agents or cofactors of severe chronic diseases like peptic ulcers or heart diseases.

Napthtyridin-2-one and quinolin-2-one antibiotic compounds have already been described in WO 2006/134378, WO 2006/137485, WO 2007/138974, WO 2008/006648, WO 2008/009700, WO 2008/071961, WO 2008/071964 and WO 2008/071981.

Quinoline, naphthyridine or quinoxaline spirooxazolidinone antibiotic compounds have besides been described in WO 2008/026172.

The Applicants have now found a new family of oxazolidinyl antibiotic compounds corresponding to the formula I described hereafter.

Various embodiments of the invention are presented hereafter:

DETAILED DESCRIPTION OF PREFERRED EMBODIMENTS i) The invention firstly relates to compounds of formula I wherein
  $R^1$ represents alkoxy (notably methoxy) or halogen (notably F);
  U and V each independently represent CH or N;
  "-----" is a bond or is absent;
  W represents CH or N or, when "-----" is absent, W represents $CH_2$ or NH,
  with the proviso that U, V and W do not all represent N;
  A represents a bond or $CH_2$;
  $R^2$ represents H or, provided A is $CH_2$, may also represent OH;
  m and n each independently represent 0 or 1;
  D represents $CH_2$ or a bond;
  G represents a phenyl group which is substituted once or twice in the meta and/or para position(s) by substituents selected from alkyl, $(C_1-C_3)$alkoxy and halogen (notably F), whereby a $(C_1-C_3)$alkoxy substituent is preferably a straight chain $(C_1-C_3)$alkoxy and in para position, or G is one of the groups $G^1$ and $G^2$ wherein
  $Z^1$, $Z^2$ and $Z^3$ each represent CH, or $Z^1$ and $Z^2$ each represent CH and $Z^3$ represents N, or $Z^1$ represents CH, $Z^2$ represents N and $Z^3$ represents CH or N, or $Z^1$ represents N and $Z^2$ and $Z^3$ each represent CH; and X represents N or CH and Q represents O or S;

it being understood that if m and n each represent 0, then A represents $CH_2$;

and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group containing from one to four carbon atoms. Representative examples of alkyl groups include methyl, ethyl, propyl, iso-propyl, n-butyl, iso-butyl, sec-butyl and tert-butyl. The term "($C_1$-$C_x$)alkyl" (x being an integer) refers to a straight or branched chain alkyl group containing 1 to x carbon atoms. Preferred alkyl groups are methyl and ethyl. The most preferred alkyl group is methyl.

The term "alkoxy", used alone or in combination, refers to a straight or branched chain alkoxy group containing from one to four carbon atoms. The term "($C_x$-$C_y$)alkoxy" (x and y each being an integer) refers to an alkoxy group as defined before containing x to y carbon atoms. For example, a ($C_1$-$C_3$)alkoxy group contains from one to three carbon atoms. Representative examples of alkoxy groups include methoxy, ethoxy, n-propoxy and iso-propoxy. Preferred are methoxy and ethoxy.

The term "halogen" refers to fluorine, chlorine, bromine or iodine, preferably to fluorine or chlorine.

In this text, a bond interrupted by a wavy line shows a point of attachment of the radical drawn to the rest of the molecule. For example, the radical drawn below

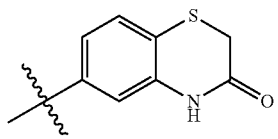 [SMILES: *c1ccc2c(c1)NC(=O)CS2]

is the 3-oxo-3,4-dihydro-2H-benzo[1,4]thiazin-6-yl group.

The present invention also includes isotopically labelled, especially $^2H$ (deuterium) labelled compounds of formula I, which compounds are identical to the compounds of formula I except that one or more atoms have each been replaced by an atom having the same atomic number but an atomic mass different from the atomic mass usually found in nature. Isotopically labelled, especially $^2H$ (deuterium) labelled compounds of formula I and salts thereof are within the scope of the present invention. Substitution of hydrogen with the heavier isotope $^2H$ (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one variant of the invention, the compounds of formula I are not isotopically labelled, or they are labelled only with one or more deuterium atoms. In a sub-variant, the compounds of formula I are not isotopically labelled at all. Isotopically labelled compounds of formula I may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) In particular, the invention relates to compounds of formula I that are also compounds of formula $I_{CE}$

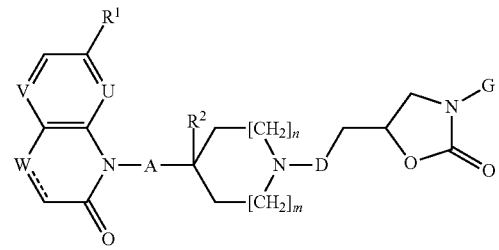

wherein $R^1$ represents alkoxy (notably methoxy);

V represents CH;

U and W each represent CH and "-----" is a bond, or U represents CH, W represents N and "-----" is a bond, or U and W each represent N and "-----" is a bond, or U represents CH, W represents $CH_2$ and "-----" is absent;

A represents a bond or $CH_2$;

$R^2$ represents H or, provided A is $CH_2$, may also represent OH;

m and n each independently represent 0 or 1;

D represents $CH_2$ or a bond;

G represents an phenyl group which is substituted once in a meta and once in the para position by substituents selected from alkyl (notably methyl) and halogen (notably F), or G is one of the groups $G^1$, and $G^2$,

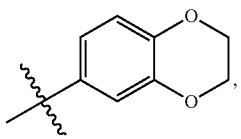

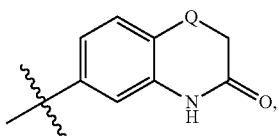

wherein Q represents O or S;

it being understood that if m and n each represent 0, then A represents $CH_2$;

and to salts (in particular pharmaceutically acceptable salts) of compounds of formula $I_{CE}$.

iii) According to a preferred embodiment of this invention, the compounds of formula I as defined in embodiment i) or ii) above will be such that $R^1$ is alkoxy or fluorine (and preferably ($C_1$-$C_3$)alkoxy, in particular methoxy or ethoxy, especially methoxy).

iv) Another embodiment of this invention relates to the compounds of formula I as defined in embodiment i), ii) or iii) above wherein "-----" is a bond.

v) According to one sub-embodiment of embodiment iv), the compounds of formula I as defined in embodiment iv) above will be such that W is CH.

vi) According to another sub-embodiment of embodiment iv), the compounds of formula I as defined in embodiment iv) above will be such that W is N.

vii) Yet another embodiment of this invention relates to the compounds of formula I as defined in embodiment i), ii) or iii) above wherein "-----" is absent.

viii) According to one sub-embodiment of embodiment vii), the compounds of formula I as defined in embodiment vii) above will be such that W is $CH_2$.

ix) According to another sub-embodiment of embodiment vii), the compounds of formula I as defined in embodiment vii) above will be such that W is NH.

x) One main variant of this invention relates to compounds of formula I as defined in one of embodiments i) to ix) wherein V is CH.

xi) According to one sub-variant of main variant x), the compounds of formula I as defined in main variant x) above will be such that U is CH.

xii) According to another sub-variant of main variant x), the compounds of formula I as defined in main variant x) above will be such that U is N.

xiii) Another main variant of this invention relates to compounds of formula I as defined in one of embodiments i) to ix) wherein V is N.

xiv) A further embodiment of this invention relates to the compounds of formula I as defined in embodiment i) to xiii) above wherein A represents a bond.

xv) Preferably, the compounds of formula I as defined in embodiment xiv) above will be such that m and n each represent 1.

xvi) Yet a further embodiment of this invention relates to the compounds of formula I as defined in embodiment i) to xiii) above wherein A represents $CH_2$.

xvii) According to one sub-embodiment of embodiment xvi), the compounds of formula I as defined in embodiment xvi) above will be such that m and n each represent 0.

xviii) According to another sub-embodiment of embodiment xvi), the compounds of formula I as defined in embodiment xvi) above will be such that one of m and n represents 0 and the other represents 1.

xix) According to yet another sub-embodiment of embodiment xvi), the compounds of formula I as defined in embodiment xvi) above will be such that m and n each represent 1.

xx) One main variant of this invention relates to the compounds of formula I as defined in one of embodiments xvi) to xix) above wherein $R^2$ represents H.

xxi) Another main variant of this invention relates to the compounds of formula I as defined in one of embodiments xvi) to xix) above wherein $R^2$ represents OH.

xxii) Yet another embodiment of this invention relates to the compounds of formula I as defined in embodiment i) to xxi) above wherein D represents $CH_2$.

xxiii) Yet another embodiment of this invention relates to the compounds of formula I as defined in embodiment i) to xxi) above wherein D represents a bond.

xxiv) One main embodiment of this invention relates to compounds of formula I as defined in one of embodiments i) to xxiii) above wherein G represents a group of the formula $G^1$, or, in the embodiments referring to embodiment ii), the group $G^{1'}$.

xxv) Preferably, the compounds of formula I as defined in embodiment xxiv) above will be such that each of $Z^1$, $Z^2$ and $Z^3$, if present, represents CH (that is, G represents 2,3-dihydrobenzo[1,4]dioxin-6-yl).

xxvi) Another main embodiment of this invention relates to compounds of formula I as defined in one of embodiments i) to xxiii) above wherein G represents a group of the formula $G^2$, or, in the embodiments referring to embodiment ii), the group $G^{2'}$.

xxvii) Preferably, the compounds of formula I as defined in embodiment xxvi) above will be such that X, if present, represents CH (that is, G represents 3-oxo-3,4-dihydro-2H-benzo[1,4]thiazin-6-yl or 3-oxo-3,4-dihydro-2H-benzo[1,4]oxazin-6-yl).

xxviii) Yet another main embodiment of this invention relates to compounds of formula I as defined in one of embodiments i) to xxiii) above either wherein G represents a phenyl group which is substituted once or twice in the meta and/or para position(s) by substituents selected independently from ($C_1$-$C_4$)alkyl, ($C_1$-$C_3$)alkoxy and a halogen (notably F), whereby a ($C_1$-$C_3$)alkoxy substituent, if present, is preferably a straight chain ($C_1$-$C_3$)alkoxy and in para position, or, in the embodiments referring to embodiment ii), wherein G represents a phenyl group which is substituted once in a meta position and once in the para position by substituents selected independently from ($C_1$-$C_4$)alkyl and a halogen (notably F).

xxix) Preferably, the compounds of formula I as defined in embodiment xxviii) above will be either such that G represents a phenyl group which is substituted once or twice in the meta and/or para position(s) by substituents selected independently from methyl, ethyl, methoxy, ethoxy and halogen (notably F), whereby a methoxy or ethoxy substituent, if present, is in para position, or, in the embodiments referring to embodiment ii), such that G represents a phenyl group which is substituted once in a meta position and once in the para position by substituents selected independently from methyl and fluorine.

xxx) In particular, the compounds of formula I as defined in embodiment xxviii) above will be such that G represents 3-fluoro-4-methyl-phenyl.

xxxi) According to one particular variant of this invention, the compounds of formula I as defined in embodiments i) to xxx) above will be such that their stereochemistry is as drawn below

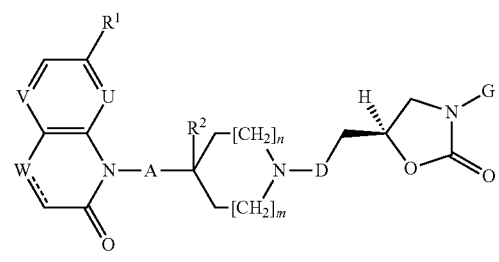

xxxii) According to another particular variant of this invention, the compounds of formula I as defined in embodiments i) to xxx) above will be such that their stereochemistry is as drawn below

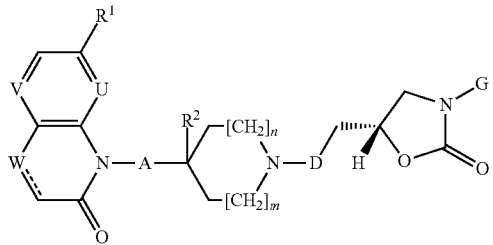

xxxiii) Particularly preferred are the following compounds of formula I as defined in embodiment i) or ii):

- 6-{(R)-5-[3-hydroxy-3-(7-methoxy-2-oxo-2H-quinolin-1-ylmethyl)-azetidin-1-ylmethyl]-2-oxo-oxazolidin-3-yl}-4H-benzo[1,4]thiazin-3-one;
- 6-{(R)-5-[3-(7-methoxy-2-oxo-2H-quinolin-1-ylmethyl)-azetidin-1-ylmethyl]-2-oxo-oxazolidin-3-yl}-4H-benzo[1,4]thiazin-3-one;
- 1-{1-[(R)-3-(2,3-dihydro-benzo[1,4]dioxin-6-yl)-2-oxo-oxazolidin-5-ylmethyl]-azetidin-3-ylmethyl}-7-methoxy-1H-quinolin-2-one;
- 6-{(R)-5-[3-(7-methoxy-2-oxo-2H-quinoxalin-1-ylmethyl)-azetidin-1-ylmethyl]-2-oxo-oxazolidin-3-yl}-4H-benzo[1,4]thiazin-3-one;
- 6-((R)-5-{2-[3-(7-methoxy-2-oxo-2H-quinolin-1-ylmethyl)-azetidin-1-yl]-ethyl}-2-oxo-oxazolidin-3-yl)-4H-benzo[1,4]thiazin-3-one;
- 6-((R)-5-{2-[3-(7-methoxy-2-oxo-2H-quinoxalin-1-ylmethyl)-azetidin-1-yl]-ethyl}-2-oxo-oxazolidin-3-yl)-4H-benzo[1,4]thiazin-3-one;
- 6-{(R)-5-[4-(7-methoxy-2-oxo-2H-quinolin-1-ylmethyl)-piperidin-1-ylmethyl]-2-oxo-oxazolidin-3-yl}-4H-benzo[1,4]thiazin-3-one;
- 1-{1-[(R)-3-(2,3-dihydro-benzo[1,4]dioxin-6-yl)-2-oxo-oxazolidin-5-ylmethyl]-piperidin-4-ylmethyl}-7-methoxy-1H-quinolin-2-one;
- 1-{1-[(R)-3-(3-fluoro-4-methyl-phenyl)-2-oxo-oxazolidin-5-ylmethyl]-piperidin-4-ylmethyl}-7-methoxy-1H-quinolin-2-one;
- 6-{(R)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]thiazin-3-one;
- 6-{(S)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]thiazin-3-one;
- 6-{(R)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]oxazin-3-one;
- 6-{(R)-5-[3-(7-methoxy-2-oxo-2H-quinoxalin-1-ylmethyl)-azetidin-1-ylmethyl]-2-oxo-oxazolidin-3-yl}-4H-benzo[1,4]oxazin-3-one;
- 1-{1-[(R)-3-(2,3-dihydro-benzo[1,4]dioxin-6-yl)-2-oxo-oxazolidin-5-ylmethyl]-azetidin-3-ylmethyl}-7-methoxy-1H-quinoxalin-2-one;
- 6-methoxy-4-{1-[(R)-2-oxo-3-(3-oxo-3,4-dihydro-2H-benzo[1,4]thiazin-6-yl)-oxazolidin-5-ylmethyl]-piperidin-4-yl}-4H-pyrido[2,3-b]pyrazin-3-one;
- 6-methoxy-4-{1-[(R)-2-oxo-3-(3-oxo-3,4-dihydro-2H-benzo[1,4]oxazin-6-yl)-oxazolidin-5-ylmethyl]-piperidin-4-yl}-4H-pyrido[2,3-b]pyrazin-3-one;
- 6-{(R)-5-[(R)-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;
- 6-{(R)-5-[3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;
- 6-{(S)-5-[3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;
- 6-((S)-5-{2-[3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one;
- 6-((R)-5-{2-[3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one;
- 4-{1-[(R)-3-(2,3-dihydro-benzo[1,4]dioxin-6-yl)-2-oxo-oxazolidin-5-ylmethyl]-piperidin-4-yl}-6-methoxy-4H-pyrido[2,3-b]pyrazin-3-one;
- 6-methoxy-4-(1-{2-[(S)-2-oxo-3-(3-oxo-3,4-dihydro-2H-benzo[1,4]thiazin-6-yl)-oxazolidin-5-yl]-ethyl}-piperidin-4-yl)-4H-pyrido[2,3-b]pyrazin-3-one;
- 4-{1-[(R)-3-(3-fluoro-4-methyl-phenyl)-2-oxo-oxazolidin-5-ylmethyl]-piperidin-4-yl}-6-methoxy-4H-pyrido[2,3-b]pyrazin-3-one;
- 6-methoxy-4-(1-{2-[(R)-2-oxo-3-(3-oxo-3,4-dihydro-2H-benzo[1,4]thiazin-6-yl)-oxazolidin-5-yl]-ethyl}-piperidin-4-yl)-4H-pyrido[2,3-b]pyrazin-3-one;

as well as the salts (in particular the pharmaceutically acceptable salts) thereof.

xxxiv) A further object of this invention thus relates to the following compounds of formula I as defined in embodiment i) or ii):

- 6-{(R)-5-[3-hydroxy-3-(7-methoxy-2-oxo-2H-quinolin-1-ylmethyl)-azetidin-1-ylmethyl]-2-oxo-oxazolidin-3-yl}-4H-benzo[1,4]thiazin-3-one;
- 6-{(R)-5-[3-(7-methoxy-2-oxo-2H-quinolin-1-ylmethyl)-azetidin-1-ylmethyl]-2-oxo-oxazolidin-3-yl}-4H-benzo[1,4]thiazin-3-one;
- 1-{1-[(R)-3-(2,3-dihydro-benzo[1,4]dioxin-6-yl)-2-oxo-oxazolidin-5-ylmethyl]-azetidin-3-ylmethyl}-7-methoxy-1H-quinolin-2-one;
- 6-{(R)-5-[3-(7-methoxy-2-oxo-2H-quinoxalin-1-ylmethyl)-azetidin-1-ylmethyl]-2-oxo-oxazolidin-3-yl}-4H-benzo[1,4]thiazin-3-one;
- 6-((R)-5-{2-[3-(7-methoxy-2-oxo-2H-quinolin-1-ylmethyl)-azetidin-1-yl]-ethyl}-2-oxo-oxazolidin-3-yl)-4H-benzo[1,4]thiazin-3-one;
- 6-((R)-5-{2-[3-(7-methoxy-2-oxo-2H-quinoxalin-1-ylmethyl)-azetidin-1-yl]-ethyl}-2-oxo-oxazolidin-3-yl)-4H-benzo[1,4]thiazin-3-one;
- 6-{(R)-5-[4-(7-methoxy-2-oxo-2H-quinolin-1-ylmethyl)-piperidin-1-ylmethyl]-2-oxo-oxazolidin-3-yl}-4H-benzo[1,4]thiazin-3-one;
- 1-{1-[(R)-3-(2,3-dihydro-benzo[1,4]dioxin-6-yl)-2-oxo-oxazolidin-5-ylmethyl]-piperidin-4-ylmethyl}-7-methoxy-1H-quinolin-2-one;
- 1-{1-[(R)-3-(3-fluoro-4-methyl-phenyl)-2-oxo-oxazolidin-5-ylmethyl]-piperidin-4-ylmethyl}-7-methoxy-1H-quinolin-2-one;
- 6-{(R)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]thiazin-3-one;
- 6-{(S)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]thiazin-3-one;

6-{(R)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]oxazin-3-one;

6-{(R)-5-[3-(7-methoxy-2-oxo-2H-quinoxalin-1-ylmethyl)-azetidin-1-ylmethyl]-2-oxo-oxazolidin-3-yl}-4H-benzo[1,4]oxazin-3-one;

1-{1-[(R)-3-(2,3-dihydro-benzo[1,4]dioxin-6-yl)-2-oxo-oxazolidin-5-ylmethyl]-azetidin-3-ylmethyl}-7-methoxy-1H-quinoxalin-2-one;

6-methoxy-4-{1-[(R)-2-oxo-3-(3-oxo-3,4-dihydro-2H-benzo[1,4]thiazin-6-yl)-oxazolidin-5-ylmethyl]-piperidin-4-yl}-4H-pyrido[2,3-b]pyrazin-3-one;

6-methoxy-4-{1-[(R)-2-oxo-3-(3-oxo-3,4-dihydro-2H-benzo[1,4]oxazin-6-yl)-oxazolidin-5-ylmethyl]-piperidin-4-yl}-4H-pyrido[2,3-b]pyrazin-3-one;

6-{(R)-5-[(R)-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;

6-{(R)-5-[(R)-3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;

6-{(R)-5-[(S)-3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;

6-{(S)-5-[(R)-3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;

6-{(S)-5-[(S)-3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;

6-((S)-5-{2-[(R)-3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one;

6-((S)-5-{2-[(S)-3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one;

6-((R)-5-{2-[(R)-3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one;

6-((R)-5-{2-[(S)-3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one;

4-{1-[(R)-3-(2,3-dihydro-benzo[1,4]dioxin-6-yl)-2-oxo-oxazolidin-5-ylmethyl]-piperidin-4-yl}-6-methoxy-4H-pyrido[2,3-b]pyrazin-3-one;

6-methoxy-4-(1-{2-[(S)-2-oxo-3-(3-oxo-3,4-dihydro-2H-benzo[1,4]thiazin-6-yl)-oxazolidin-5-yl]-ethyl}-piperidin-4-yl)-4H-pyrido[2,3-b]pyrazin-3-one;

4-{1-[(R)-3-(3-fluoro-4-methyl-phenyl)-2-oxo-oxazolidin-5-ylmethyl]-piperidin-4-yl}-6-methoxy-4H-pyrido[2,3-b]pyrazin-3-one;

6-methoxy-4-(1-{2-[(R)-2-oxo-3-(3-oxo-3,4-dihydro-2H-benzo[1,4]thiazin-6-yl)-oxazolidin-5-yl]-ethyl}-piperidin-4-yl)-4H-pyrido[2,3-b]pyrazin-3-one;

as well as the salts (in particular the pharmaceutically acceptable salts) thereof.

xxxv) The invention in particular relates to the groups of compounds of formula I selected from the compounds listed in embodiment xxxiii), which groups of compounds furthermore correspond to one of embodiments iii) to xxxii), as well as to the salts (in particular the pharmaceutically acceptable salts) of such compounds.

xxxvi) The invention also relates to the groups of compounds of formula I selected from the compounds listed in embodiment xxxiv), which groups of compounds furthermore correspond to one of embodiments iii) to xxxii), as well as to the salts (in particular the pharmaceutically acceptable salts) of such compounds.

The compounds of formula I according to the invention, i.e. according to one of embodiments i) to xxxvi), are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C—F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M leprae, M paratuberculosis, M kansasii*, or *M chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp. including *Acinetobacter baumanii, Stenothrophomonas maltophilia, Neisseria meningitidis, Bacillus cereus, Bacillus anthracis, Clostridium difficile, Corynebacterium* spp., *Propionibacterium acnes* and bacteroide spp.

The compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of fomula I according to this invention, i.e. according to one of embodiments i) to xxxvi) above, or the pharmaceutically acceptable salts thereof, may be used for the preparation of a medicament, and are suitable, for the prevention or treatment (and notably for the treatment) of a bacterial infection.

One aspect of this invention therefore relates to the use of a compound of formula I according to one of embodiments i) to xxxvi), or of a pharmaceutically acceptable salt thereof, for the manufacture of a medicament for the prevention or treatment (and notably for the treatment) of a bacterial infection. Another aspect of this invention relates to a compound of formula I according to one of embodiments i) to xxxvi), or of a pharmaceutically acceptable salt thereof, for the prevention or treatment (and notably for the treatment) of a bacterial infection.

Accordingly, the compounds of formula I according to one of embodiments i) to xcv), or the pharmaceutically acceptable salts thereof, may be used for the preparation of a medicament, and are suitable, for the prevention or treatment (and notably for the treatment) of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably for the prevention or treatment (especially for the treatment) of a bacterial infection selected from the group consisting of respiratory tract infections, otitis media, meningitis, skin and soft tissue infections (whether complicated or uncomplicated), pneumonia (including hospital acquired pneumonia) and bacteremia.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I in this text (and notably in the embodiments presented above) is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment (and notably for the treatment) of a bacterial infection in a patient comprising the administration to said patient of a pharmaceutically active amount of a compound of formula I according to one of embodiments i) to xxxvi) or a pharmaceutically acceptable salt thereof.

Besides, any preferences and (sub-)embodiments indicated for the compounds of formula I (whether for the compounds themselves, salts thereof, compositions containing the compounds or salts thereof, uses of the compounds or salts thereof, etc.) apply mutatis mutandis to compounds of formula $I_{CE}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

PREPARATION OF COMPOUNDS OF FORMULA I

Abbreviations:
The following abbreviations are used throughout the specification and the examples:
Ac acetyl
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
aq. aqueous
Boc tert-butoxycarbonyl
Bs 4-bromophenylsulfonyl
Cbz benzyloxycarbonyl
CC column chromatography over silica gel
CDI 1,1'-carbonyldiimidazole
DCM dichloromethane
DIPEA N,N-diisopropylethylamine
DMAP 4-dimethylaminopyridine
DMF N,N-dimethylformamide
DMSO dimethylsulfoxide
EA ethyl acetate
ESI Electron Spray Ionisation
eq. equivalent
ether diethyl ether
Et ethyl EtOH ethanol
Fmoc 9-fluorenylmethoxycarbonyl
Hex hexane
Hept heptane
HV high vacuum conditions
KHMDS potassium hexamethyldisilazide
LC liquid chromatography
MCPBA meta-chloroperbenzoic acid
Me methyl
MeCN acetonitrile
MeOH methanol
MS Mass Spectroscopy
Ms methanesulfonyl (mesyl)
n-BuLi n-butyl lithium
Nf nonafluorobutanesulfonyl
NMO N-methyl-morpholine N-oxide
Ns 3-nitrophenylsulfonyl
org. organic
Pd/C palladium on carbon
Pd(OH)$_2$/C palladium dihydroxide on carbon
Ph phenyl
Pyr pyridine
rac racemic
rt room temperature
sat. saturated
TBAF tetrabutylammonium fluoride
TBDMS tert-butyldimethylsilyl
TBDPS tert-butyldiphenylsilyl
TBME tert-butylmethylether
TEA triethylamine
Tf trifluoromethanesulfonyl (triflyl)
TFA trifluoroacetic acid
THF tetrahydrofuran
TLC thin layer chromatography
Ts para-toluenesulfonyl
General Reaction Techniques:
General Reaction Technique 1 (Alkylation of an Amine):

The appropriate amine derivatives are reacted with the appropriate derivatives containing a group $Y^1$, $Y^2$ or $Y^3$, wherein $Y^1$, $Y^2$ and $Y^3$ each independently represent OMs, ONf, ONs, OBs, OTf, OTs, Cl, Br or I in presence of an inorganic base such as $K_2CO_3$ or an org. base such as TEA in a solvent such as THF, DMF or DMSO between 0° C. and +80° C. Further details can be found in *Comprehensive Organic Transformations. A guide to Functional Group Preparations*; $2^{nd}$ Edition, R. C. Larock, Wiley-VC; New York, Chichester, Weinheim, Brisbane, Singapore, Toronto, (1999). Section Amines p. 779.

General Reaction Technique 2 (Removal of Amino Protecting Groups);

The benzyl carbamates are deprotected by hydrogenolysis over a noble metal catalyst (e.g. Pd/C or Pd(OH)$_2$/C). The Boc group is removed under acidic conditions such as HCl in an organic solvent such as MeOH or dioxane, or TFA neat or diluted in a solvent such as DCM. Further general methods to remove amine protecting groups have been described in T. W. Greene, P. G. M. Wuts, *Protecting Groups in Organic Synthesis*, $3^{rd}$ Ed (1999), 494-653 (Publisher: John Wiley and Sons, Inc., New York, N.Y.).

General Reaction Technique 3 (Removal of Hydroxy Protecting Groups):

The silyl ether groups are removed either using fluoride anion sources such as TBAF in THF between 0° C. and +40° C. or HF in MeCN between 0° C. and +40° C. or using acidic conditions such as AcOH in THF/MeOH or HCl in MeOH. Further methods to remove the TBDMS and TBDPS groups are given in T. W. Greene, P. G. M. Wuts, *Protecting Groups in Organic Synthesis*, $3^{rd}$ Ed (1999), 133-139 and 142-143 respectively (Publisher: John Wiley and Sons, Inc., New York, N.Y.). Further general methods to remove alcohol protecting groups are described in T. W. Greene, P. G. M. Wuts, *Protecting Groups in Organic Synthesis*, $3^{rd}$ Ed (1999), 23-147 (Publisher: John Wiley and Sons, Inc., New York, N.Y.). In the particular case of alkylcarboxy protecting group, the free alcohol can be obtained by the action of an inorganic base such as $K_2CO_3$ in a solvent such as MeOH.

General Reaction Technique 4 (Activation of an Alcohol):

The alcohol is reacted with BsCl, MsCl, NfCl, NsCl, TfCl or TsCl in presence of an organic base such as TEA, DIPEA or Pyr in a dry aprotic solvent such as DCM, THF or Pyr between −10° C. and rt. Alternatively, the alcohol can also be reacted with Ms$_2$O or Tf$_2$O. The activated intermediate can be further transformed into its corresponding iodo or bromo derivative by reaction of the activated alcohol with NaI or NaBr in a solvent such as acetone.

General Reaction Technique 5 (Oxidation of Alcohols):

The alcohols can be transformed into their corresponding aldehydes or ketones through oxidation under Swern (see D. Swern et al., *J. Org. Chem*. (1978), 43, 2480-2482) or Dess-Martin (see D. B. Dess and J. C. Martin, *J Org. Chem*. (1983), 48, 4155) conditions respectively.

General Reaction Technique 6 (cis-dihydroxylation):

The diol is obtained by dihydroxylation of the corresponding ethylenic derivative using a catalytic amount of osmium tetroxide in the presence a co-oxidant such as NMO in an aq. solvent such as an acetone-water or DCM-water mixture (see Cha, J. K. *Chem. Rev*. (1995), 95, 1761-1795). The chiral cis-diols are obtained by using AD-mix cc or AD-mix β in presence of methanesulfonamide in a water/2-methyl-2 propanol mixture as described in *Chem. Rev*. (1994), 94, 2483. The sense of induction relies on the chiral ligand contained in the AD mixture, either a dihydroquinine-based ligand in AD-mix α or a dihydroquinidine-based ligand in AD-mix β.

General Reaction Technique 7 (Protection of Alcohols):

The alcohols are protected as silyl ethers (usually TBDMS or TBDPS ethers). The alcohol is reacted with the required silyl chloride reagent (TBDMSCl or TBDPSCl) in presence of a base such as imidazole or TEA in a solvent such as DCM or DMF between +10° C. and +40° C. Further strategies to introduce other alcohol protecting groups have been described in T. W. Greene, P. G. M. Wuts, *Protecting Groups in Organic Synthesis*, 3rd Ed (1999), 23-147 (Publisher: John Wiley and Sons, Inc., New York, N.Y.).

General Reaction Technique 8 (Hydrogenation of a Double Bond):

The unsaturated derivatives dissolved in a solvent such as MeOH, EA or THF are hydrogenated over a noble metal catalyst such as Pd/C or platinum, or over Raney Ni. At the end of the reaction the catalyst is filtered off and the filtrate is evaporated under pressure. Alternatively the reduction can be performed by catalytic transfer hydrogenation using Pd/C and ammonium formate as hydrogen source.

General Preparation Methods:
Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to f) hereafter describe general methods for preparing compounds of formula I. In these sections, unless indicated otherwise, the generic groups or integers m, n, $R^1$, $R^2$, A, B, D, U, V, W, G and Q and the optional bond "-----" are as defined for formula I. Other abbreviations used are defined in the experimental section. In some instances the generic groups U, V, W, R² and G might be incompatible with the assembly illustrated in the procedures and schemes below and so will require the use of protecting groups. The use of protecting groups is well known in the art (see for example "Protective Groups in Organic Synthesis", T. W. Greene, P. G. M. Wuts, Wiley-Interscience, 1999).

a) The compounds of formula I can be manufactured by reacting the compounds of formula II

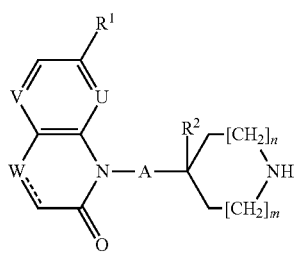

II with the compounds of formula III

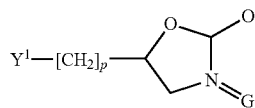

III wherein Y¹ is a halogen such as bromine or iodine, or a group $OSO_2R^a$ wherein $R^a$ is alkyl, $CF_3$ or tolyl and p is 1 or 2, following general reaction technique 1.

b) The compounds of formula I can be obtained by reacting the compounds of formula IV

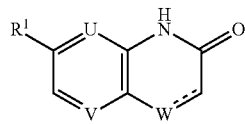

IV with the compounds of formula V

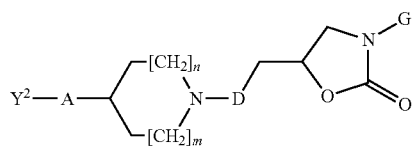

V wherein Y² is a halogen such as bromine or iodine, or a group $OSO_2R^a$ wherein $R^a$ is alkyl, $CF_3$ or tolyl, following general reaction technique 1.

c) The compounds of formula I wherein A is $CH_2$ and R² is OH can be obtained by reacting the compounds of formula IV as defined in section b) above with the compounds of formula VI

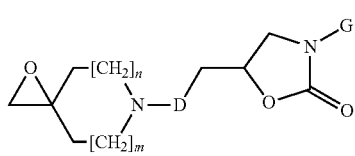

VI in the presence of $Cs_2CO_3$ or NaH in a polar solvent such as DMF between 60° C. and 140° C.

d) The compounds of formula I wherein W is N and "-----" is a bond can be obtained by reacting the compounds of formula VII

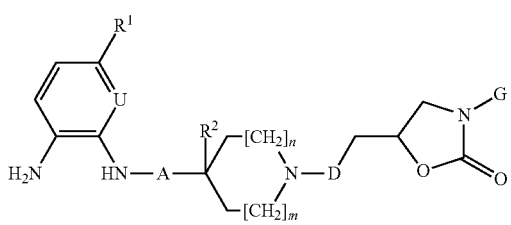

VII with the compounds of formula $CHOCOOR^b$ wherein $R^b$ is alkyl, or with alkyl bromoacetate in presence of a base such as $K_2CO_3$ followed by cyclization in acidic media such as AcOH in hot toluene and aromatisation by treatment with $MnO_2$ or $H_2O_2$.

e) The compounds of formula I can besides be obtained by reacting the compounds of formula VIII

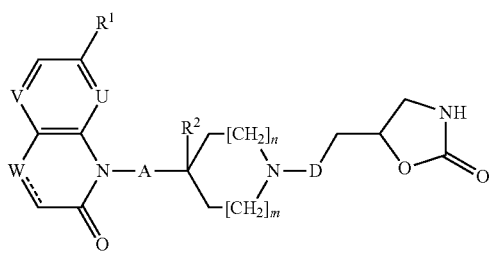

VIII with the compounds of formula IX

G-X<sup>a</sup>  IX wherein $X^a$ represents OTf or halogen such as chlorine, bromine or iodine. This reaction can be performed under conditions described for the metal catalysed N-arylation of 2-oxazolidinones or amides, in particular using CuI and 1,1,1-tris(hydroxymethyl)ethane in presence of $Cs_2CO_3$ (*Org. Lett.* (2006), 8, 5609-5612), or $Pd(OAc)_2$ and DPEphos in presence of $K_3PO_4$, and be followed, if necessary, by removal of the protecting group $PG^0$ according to general reaction technique 2.

f) The compounds of formula I wherein W is $CH_2$ or NH and "-----" is absent can be obtained by hydrogenation of the corresponding compounds of formula I wherein "-----" is a bond following general reaction technique 8 or by reduction of the same using NaBH$_4$ in a solvent such as EtOH.

The compounds of formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min. Whenever the compounds of formula I are obtained in the form of mixtures of diasteromers they may be separated by an appropriate combination of silica gel chromatography, HPLC and crystallization techniques.

Preparation of the Compounds of Formulae II to IX:

The compounds of formula II can be prepared as described in Scheme 1 hereafter.

reacted with the compounds of formula IV (general reaction technique 1). The amino protecting group in intermediate I-2 can then be removed (general reaction technique 2) to yield the compounds of formula II. The compounds of formulae I-2 and II wherein "-----" is absent can be obtained by hydrogenation of the compounds of formulae I-2 and II wherein "-----" is a bond or by reduction of the same using NaBH$_4$ in a solvent such as EtOH.

The compounds of formula III can be prepared as described in Scheme 2 hereafter.

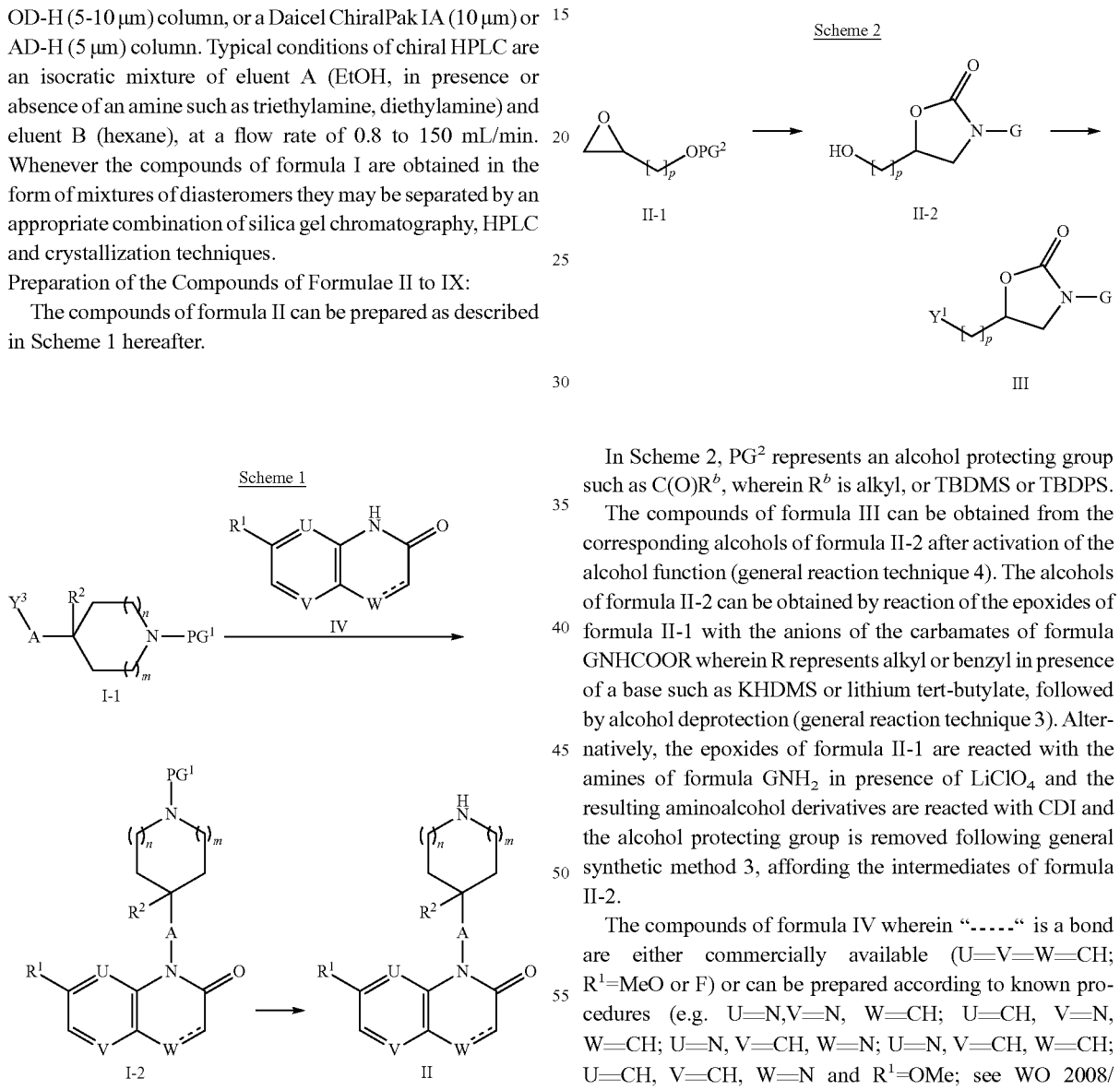

In Scheme 1, $Y^3$ is a halogen such as bromine or iodine, or a group OSO$_2$R$^a$ wherein R$^a$ is alkyl, CF$_3$ or tolyl and PG$^1$ is an amino protecting group such as Cbz, Boc or Fmoc.

The compounds of formula I-1, wherein A is CH$_2$ or a bond and R$^2$ is H or, provided A is CH$_2$, R$^2$ may also be OH, can be In Scheme 2, PG$^2$ represents an alcohol protecting group such as C(O)R$^b$, wherein R$^b$ is alkyl, or TBDMS or TBDPS.

The compounds of formula III can be obtained from the corresponding alcohols of formula II-2 after activation of the alcohol function (general reaction technique 4). The alcohols of formula II-2 can be obtained by reaction of the epoxides of formula II-1 with the anions of the carbamates of formula GNHCOOR wherein R represents alkyl or benzyl in presence of a base such as KHDMS or lithium tert-butylate, followed by alcohol deprotection (general reaction technique 3). Alternatively, the epoxides of formula II-1 are reacted with the amines of formula GNH$_2$ in presence of LiClO$_4$ and the resulting aminoalcohol derivatives are reacted with CDI and the alcohol protecting group is removed following general synthetic method 3, affording the intermediates of formula II-2.

The compounds of formula IV wherein "-----" is a bond are either commercially available (U=V=W=CH; R$^1$=MeO or F) or can be prepared according to known procedures (e.g. U=N,V=N, W=CH; U=CH, V=N, W=CH; U=N, V=CH, W=N; U=N, V=CH, W=CH; U=CH, V=CH, W=N and R$^1$=OMe; see WO 2008/009700, WO 2006/134378 and J. Heterocycl. Chem. (1986), 23(2), 501-504). The compounds of formula IV wherein wherein U=V=W=CH and "-----" is absent can be prepared according to WO 2006/134378 or in analogy to WO 2006/090272.

The compounds of formula V can be prepared as described in Scheme 3 hereafter.

Scheme 3

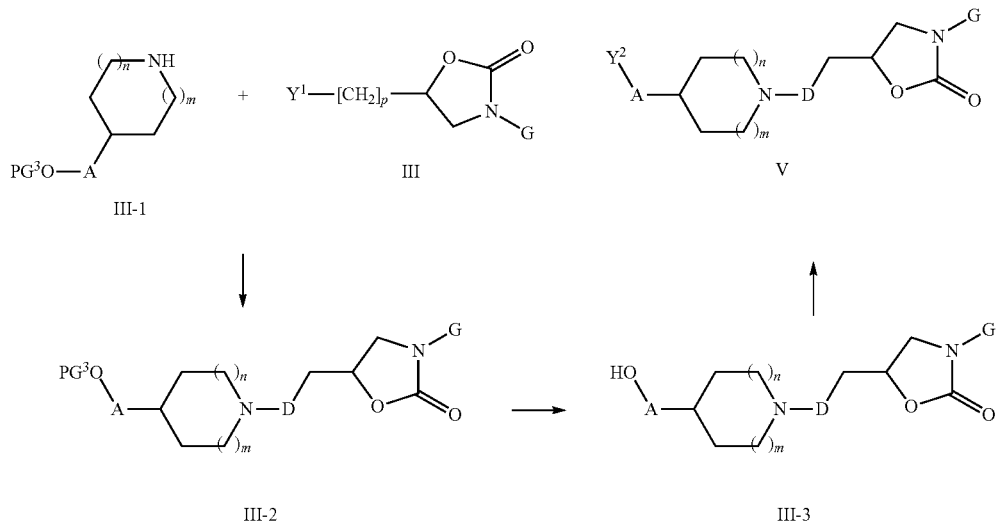

In Scheme 3, PG³ represents an alcohol protecting group such as TBDMS or TBDPS.

The compounds of formula III-1 can be reacted with the compounds of formula III (general reaction technique 1). The alcohol protecting group in intermediates of formula III-2 can be removed (general reaction technique 3). The resulting alcohol derivatives of formula III-3 can then be transformed into their corresponding activated intermediates of formula V (general reaction technique 4).

The compounds of formula VI can be prepared as described in Scheme 4 hereafter.

The alcohols of formula IV-1 (i.e. the compounds of formula III-3 of Scheme 3 wherein A is a bond) can be oxidized into their corresponding ketone analogues of formula IV-2 (general reaction technique 5). These ketones can then be transformed into the corresponding epoxide derivatives of formula VI, either through direct epoxidation with trimethylsulfonium iodide or through sequential Wittig reaction with methylene triphenylphosphorane followed by epoxidation of the intermediates of formula IV-3 with MCPBA.

The compounds of formula VII can be prepared as described in Scheme 5 hereafter.

Scheme 4

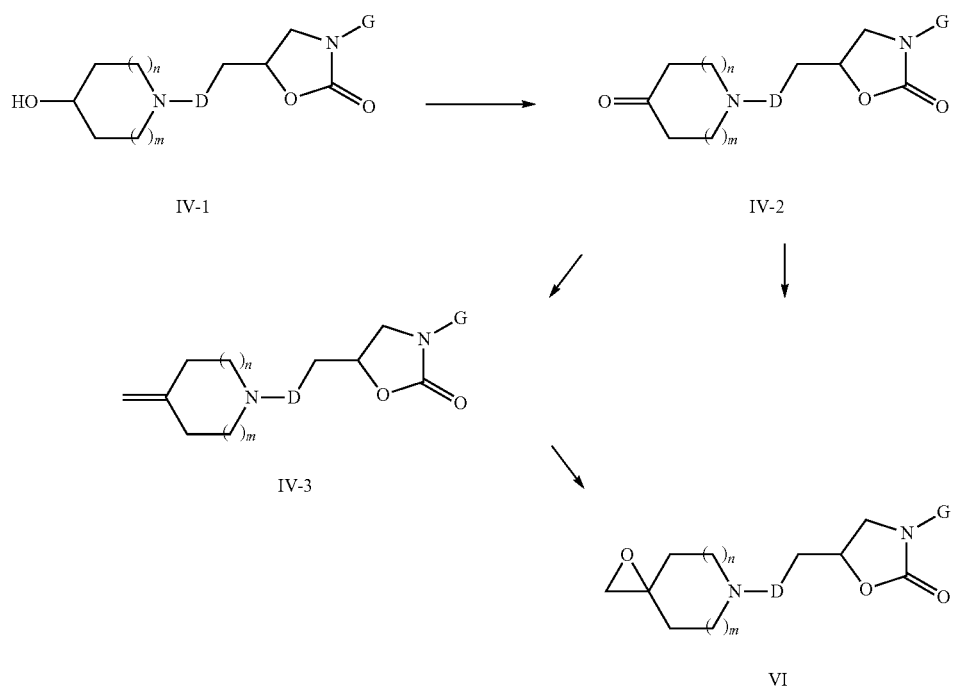

Scheme 5

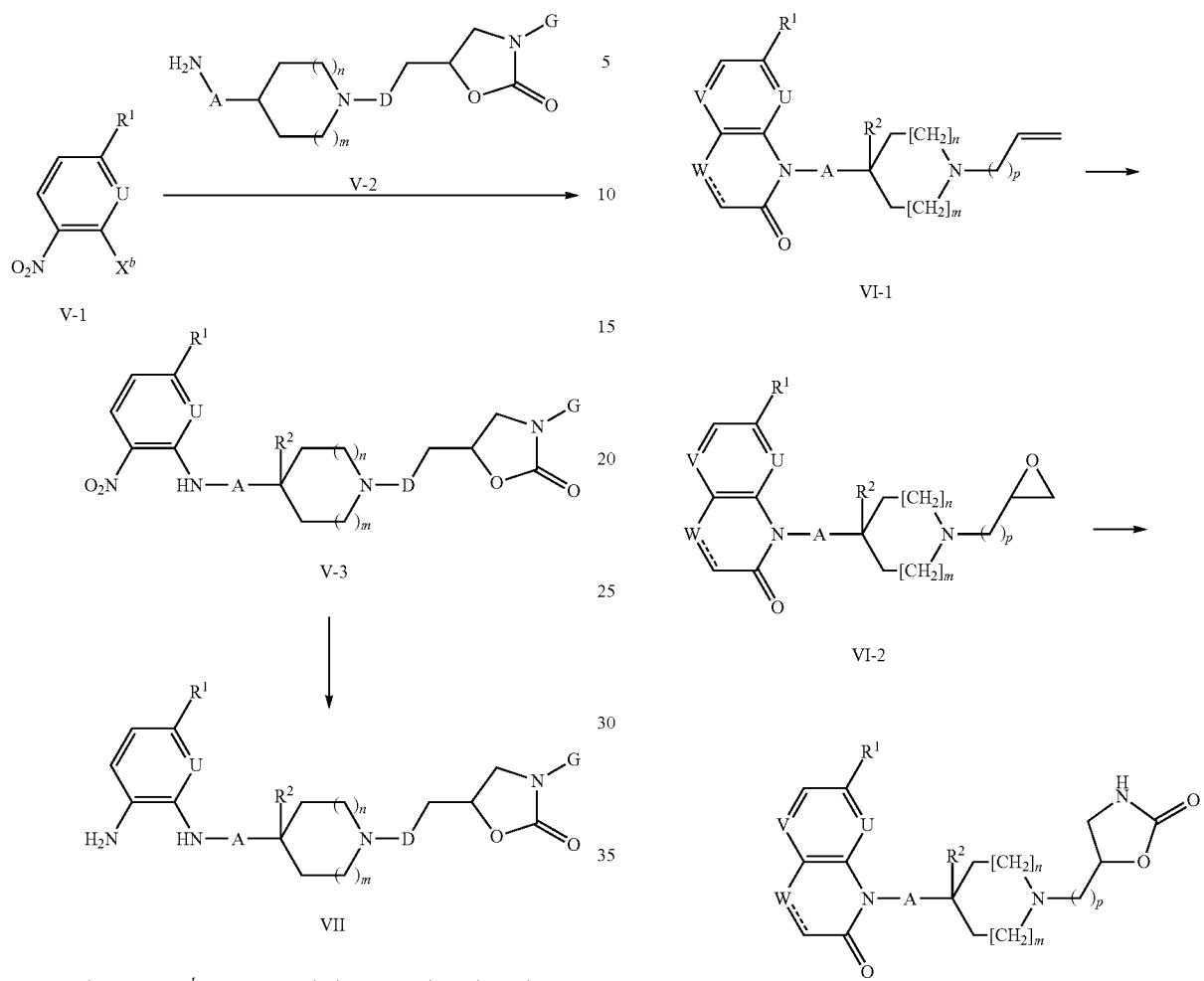

In Scheme 5, $X^b$ represents halogen such as bromine or chlorine.

The nitro derivatives of formula V-1 can be reacted with the intermediates of formula V-2. The resulting intermediates of formula V-3 can then be reduced into the corresponding amine derivatives of formula VII by hydrogenation over a noble metal catalyst such as Pd/C or Raney nickel. Further methods for nitro reduction are given in *Comprehensive Organic Transformations. A guide to Functional Group Preparations;* $2^{nd}$ Edition, R. C. Larock, Wiley-VC; New York, Chichester, Weinheim, Brisbane, Singapore, Toronto, (1999). Section Amines; p. 821.

The compounds of formula VIII can be prepared as described in Scheme 6 hereafter.

Scheme 6

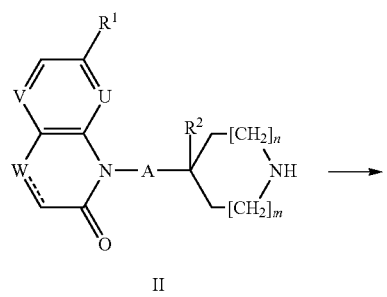

In Scheme 6, p represents 1 or 2.

Accordingly, the intermediates of formula II can be reacted with allyl or homoallyl bromide following general reaction technique 1. The intermediates of formula VI-1 can then sequentially be dihydroxylated following general reaction technique 6, activated as monomesylates following general reaction technique 4 and ring closed in presence of a base such as $K_2CO_3$ in a solvent such as MeOH or TEA. The resulting epoxides of formula VI-2 can be reacted with sodium azide followed either by hydrogenation over a noble metal catalyst such as Pd/C or by reaction with $PPh_3$ in presence of water. The resulting intermediate amines can then be transformed into their corresponding carbamates with benzyl or alkyl chloroformates and the oxazolidinones of formula VIII can be obtained after treatment with NaH.

Some compounds of formula IX are commercially available (e.g. the compounds wherein $G=G^2$, Q=O and Z=N: CAS 337463-99-7; $G=G^2$, Q=S and Z=CH: CAS 6376-70-1; $G=G^2$, Q=O and Z=CH: CAS 7652-29-1).

The compound of formula IX wherein G is $G^2$, Z is N, Q is S and $X^a$ is Cl can be obtained as summarised in Scheme 7 hereafter.

Scheme 7

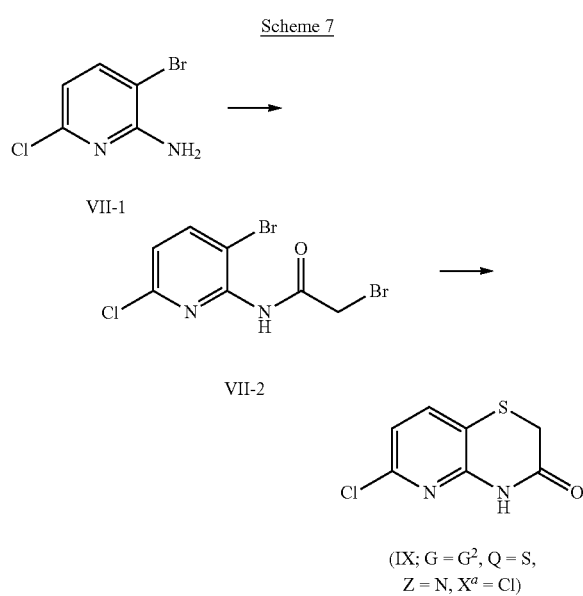

Accordingly, the bromo derivative of formula VII-1, prepared according to WO 2008/065198, can be reacted with bromoacetyl bromide and the resulting derivative of formula VII-2 can then be reacted with sodium thioacetate in presence of NaOMe, affording the compound of formula IX wherein G is $G^2$, Z is N, Q is S and $X^a$ is Cl.

The compounds of formula IX wherein G is $G^2$, X is CH, Q is O or S and $Y^4$ is OTf and those wherein G is $G^1$, each of $Z^1$, $Z^2$ and $Z^3$ is CH and $Y^4$ is OTf can be obtained from the corresponding alcohol precursors ($X^a$=OH) and $Tf_2O$ following general reaction technique 4. The latter compounds are either commercially available (CAS 53412-38-7; CAS 10288-72-9) or can be prepared as described in EP 106 816.
Preparation of Certain Intermediates:

The compounds of formula I-1 can be obtained as described in Scheme 6 hereafter.

technique 5), Wittig reaction with methylene triphenylphosphorane followed by cis-dihydroxylation (general reaction technique 6).

The compounds of formula II-1 wherein p is 1 and $PG^2$ is $C(O)R^b$, $R^b$ being alkyl, are commercially available. The compound of formula II-1 wherein p is 2 and $PG^2$ is TBDMS can be prepared according to WO 2007/144423 or EP 518672.

The compounds of formula III-1 can be obtained by protection of the alcohol function of compounds of formula VIII-1 (general reaction technique 7) and removal of the amino protecting group (general reaction technique 2).

The compounds of formula IV-1 correspond to compounds of formula III-3 wherein A is a bond.

The compounds of formula V-1 wherein $X^b$ is bromine, $R^1$ is methoxy or fluorine and U is N or CH are commercially available.

The compounds of formula V-2 can be obtained from the compounds of formula V wherein $Y^2$ is halogen such as iodine or $OSO_2Ra$ wherein Ra is alkyl, $CF_3$ or tolyl by reaction with $NaN_3$ followed by reduction with $PPh_3$ in presence of water.

Particular embodiments of the invention are described in the following Examples, which serve to illustrate the invention in more detail without limiting its scope in any way.

EXAMPLES

All temperatures are stated in °C. Compounds are characterized by $^1$H-NMR (300 MHz) (Varian Oxford); or by $^1$H-NMR (400 MHz) (Bruker Advance 400). Chemical shifts are given in ppm relative to the solvent used; multiplicities: s=singlet, d=doublet, t=triplet, q=quadruplet, p=pentuplet, hex=hexet, hep=heptet, m=multiplet, br.=broad, coupling constants are given in Hz. Alternatively compounds are characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point. Compounds are purified by chromatography on Silica gel 60A. $NH_4OH$ as used for CC is 25% aq.

Scheme 8

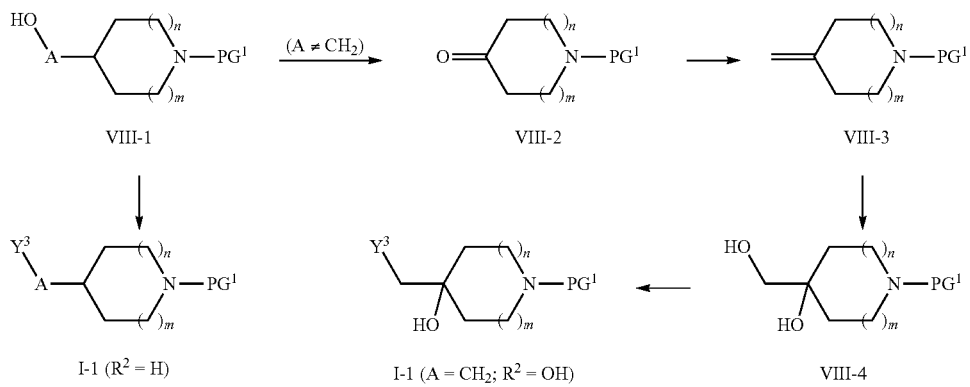

The compounds of formula I-1 can be obtained from the corresponding alcohols of formula VIII-1 or VIII-4 using general reaction technique 4 (see Scheme 8). The starting alcohols of formula VIII-1 are commercially available. The starting alcohols of formula VIII-4 can be obtained from the alcohols of formula VIII-1 after oxidation (general reaction The HPLCs are done over a stationary phase such as a rapid resolution Zorbax SB C18 (1.8 μm) column, or a rapid resolution Zorbax Eclipse Plus C18 (1.8 μm) column Typical conditions of HPLC are a gradient of eluent A (water: acetonitrile 95:5 with 0.1% of formic acid, in presence or not of 5 mmol/L ammonium formate) and eluent B (acetonitrile:

water 95:5 with 0.1% of formic acid, in presence or not of 5 mmol/L ammonium formate), at a flow rate of 0.8 to 5 mL/min. Racemates can be separated into their enantiomers as described before. Preferred conditions of chiral HPLC are: ChiralPak AD (4.6×250 mm, 5 μm) column, using an isocratic mixture (e.g. at a ratio of 10/90) of eluent A (EtOH, in presence of diethylamine in an amount of e.g. 0.1%) and eluent B (Hex), at rt, at a flow rate of e.g. 0.8 mL/min.

General Procedures:

Procedure A: Boc Deprotection:

The Boc protected amine (1 mmol) is dissolved in DCM (5 mL) and treated with Et$_3$SiH (optional; 0.2 mL, 1.1 eq.) and TFA (2 mL). The mixture is stirred at rt for 1 h, concentrated in vacuo and taken up in DCM/aq. NH$_4$OH. The org. layer is washed with water, dried over MgSO$_4$ and concentrated under reduced pressure.

Procedure B: Alkylation of Amines with Iodides:

A solution of amine (1 mmol), iodide (1 mmol) and DIPEA (1.1 mmol) in dry DMSO is heated to 70° C. until completion of the reaction (1-3 days). After cooling, water and EA are added and the phases are separated. The aq. layer is extracted two more times with EA and the combined org. layers are washed with water (3×) and brine, dried over MgSO$_4$ and concentrated under reduced pressure. The residue is then purified by CC.

Procedure C: Alkylation of Amines with Mesylates:

A solution of the amine (1.0-2.3 mmol), the mesylate (1 mmol) and DIPEA (1.1 mmol) in dry DMSO is heated to 70° C. until completion of the reaction (2-5 days). After cooling, water and EA are added and the phases are separated. The aq. layer is extracted two more times with EA and the combined org. layers are washed with water (3×) and brine, dried over MgSO$_4$ and concentrated under reduced pressure. The residue is then purified by CC.

Preparation A: 6-((S)-5-iodomethyl-2-oxo-oxazolidin-3-yl)-4H-benzo[1,4]thiazin-3-one:

A.i. 6-((S)-3-chloro-2-hydroxy-propylamino)-4H-benzo[1,4]thiazin-3-one:

A suspension of 6-amino-4H-benzo[1,4]thiazin-3-one (18.0 g, 100 mmol; commercial) and Ca(OTf)$_2$ (0.5 eq.) in MeCN (800 mL) was heated at 50° for 1 h. (S)-epichlorohydrin (18.5 g, 200 mmol) was added and the mixture was stirred at rt for 72 h and at 45° C. for 24 h. The volatiles were removed under reduced pressure. After aqueous workup and extraction with EA, the title intermediate crystallized from EA to afford a beige solid (17.38 g, 64% yield).

MS (ESI, m/z): 273.2 [M+H$^+$].

A.ii. 6-((S)-5-chloromethyl-2-oxo-oxazolidin-3-yl)-4H-benzo[1,4]thiazin-3-one:

A solution of intermediate A.i (39.3 g, 144 mmol) and CDI (28.0 g, 1.2 eq.) in THF (1 L) was heated at 50° C. overnight. The mixture was concentrated under reduced pressure and partitioned between EA and water. The aq. layer was extracted once more with EA and the combined org. layers were dried over MgSO$_4$ and concentrated. The residue was purified by CC (EA/Hept 2:1, EA) to afford the title intermediate as a beige solid (34.2 g, 79% yield).

MS (ESI, m/z): 299.1 [M+H$^+$].

A.iii. 6-((S)-5-iodomethyl-2-oxo-oxazolidin-3-yl)-4H-benzo[1,4]thiazin-3-one:

A mixture of intermediate A.ii (14.0 g, 46.9 mmol) and NaI (3 eq.) in 2-butanone (150 mL) was heated at 85° C. for 2 days. After cooling to rt, the mixture was diluted with 10% aq. Na$_2$S$_2$O$_3$ (300 mL) and ether/EA (150 mL). The mixture was vigorously stirred for 10 min and filtered. The solids were thoroughly washed with water and ether and dried under HV to afford a pale beige solid. The phases of the combined filtrates were separated and the org. phase washed with brine, dried over MgSO$_4$ and concentrated to afford a pale beige solid. The solids of both processes were combined to afford the title compound as a pale beige solid (15.0 g, 82% yield).

MS (ESI, m/z): 391.4 [M+H$^+$].

Preparation B: (S)-3-(2,3-dihydro-benzo[1,4]dioxin-6-yl)-5-iodomethyl-oxazolidin-2-one:

B.i. (S)-3-(2,3-dihydro-benzo[1,4]dioxin-6-yl)-5-hydroxymethyl-oxazolidin-2-one:

A solution of (2,3-dihydro-benzo[1,4]dioxin-6-yl)-carbamic acid benzyl ester (13.0 g, 45.6 mmol) in THF (220 mL) was cooled to −78° C. before the drop wise addition of n-BuLi (29.5 mL of a 2.36M solution in hexanes, 1.1 eq). The mixture was stirred at −78° C. for 1 h and then warmed to −15° C. At this temperature (S)-glycidyl butyrate (7.37 g, 1.1 eq) was added dropwise. The mixture was stirred at rt overnight. Cs$_2$CO$_3$ (tip of a spatula) was added and the mixture heated at 40° C. until complete conversion. The mixture was diluted with EA and washed with a sat. aq. NH$_4$Cl and water. The org. layer was dried over MgSO$_4$ and concentrated. The residue was purified by CC (Hex/EA 2:1, 1:1) to afford the title intermediate as a grey solid (7.04 g, 62% yield).

$^1$H NMR (DMSO-d6) δ: 7.13 (d, J=2.5 Hz, 1H), 6.96 (dd, J=2.5, 8.9 Hz, 1H), 6.86 (d, J=8.9 Hz, 1H), 5.16 (t, J=5.8 Hz, 1H), 4.70-4.50 (m, 1H), 4.30-4.10 (m, 4H), 4.10-3.90 (m, 1H), 4.80-4.70 (m, 1H), 4.70-4.60 (m, 1H), 4.60-4.50 (m, 1H).

B.ii. Methanesulfonic acid (S)-3-(2,3-dihydro-benzo[1,4]dioxin-6-yl)-2-oxo-oxazolidin-5-ylmethyl ester:

A solution of intermediate B.i (7.0 g, 27.9 mmol) in DCM (140 mL) was cooled to 0° C. DIPEA (5.70 mL, 1.2 eq.) and MsCl (2.40 mL, 1.1 eq.) were added and the mixture was stirred for 1 h at 0° C. The mixture was diluted with DCM and washed with water. The org. phase was dried over MgSO$_4$ and concentrated to give the title intermediate as a colourless solid (9.0 g, 98% yield).

MS (ESI, m/z): 330.3 [M+H$^+$].

B.iii. (S)-3-(2,3-dihydro-benzo[1,4]dioxin-6-yl)-5-iodomethyl-oxazolidin-2 one:

A mixture of intermediate B.ii (9.0 g, 27.3 mmol) and NaI (16.4 g, 4 eq.) in acetone (150 mL) was heated at reflux for 20 h. The solvent was evaporated and the residue extracted with water/DCM. The org. layer was washed with brine, dried over MgSO$_4$ and concentrated under reduced pressure. The residue was triturated with ether/EA to afford the title compound as an off-white solid (6.91 g, 70% yield).

$^1$H NMR (CDCl$_3$) δ: 7.07 (d, J=2.6 Hz, 1H), 6.98 (dd, J=9.1, 2.6 Hz, 1H), 6.85 (d, J=8.9 Hz, 1H), 4.68 (m, 1H), 4.24 (s, 4H), 4.10 (t, J=9.1 Hz, 1H), 3.72 (dd, J=9.1, 5.9 Hz, 1H), 3.46 (m, 1H), 3.33 (m, 1H).

MS (ESI, m/z): 362.2 [M+H$^+$].

Preparation C: 6-[(R)-5-(2-iodo-ethyl)-2-oxo-oxazolidin-3-yl]-4H-benzo[1,4]thiazin-3-one:

C.i. (2R)-tert-butyl-dimethyl-(2-oxiranyl-ethoxy)-silane and (2S)-4-(tent-butyl-dimethylsilanyloxy)-butane-1,2-diol:

The title intermediates were prepared in analogy to Kishi et al., Org. Lett. (2005), 7, 3997, (intermediate S2-3) via hydrolytic kinetic resolution of (RS)-tert-butyl-dimethyl-(2-oxiranyl-ethoxy)-silane (prepared according to J. Org. Chem. (2008), 73, 1093). Two compounds were isolated after CC (Hept/EA 2:1).

First eluting compound: (2R)-tert-butyl-dimethyl-(2-oxiranyl-ethoxy)-silane (colourless oil; 25.3 g, 48% yield): $^1$H NMR (CDCl$_3$) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).

Second eluting compound: (2S)-4-(tert-butyl-dimethyl-silanyloxy)-butane-1,2-diol (colourless oil; 24.9 g, 43% yield): $^1$H NMR (CDCl$_3$) δ: 3.89 (m, 3H), 3.62 (s, 1H), 3.53 (m, 1H), 3.42 (br. s, 1H), 2.29 (m, 1H), 1.70 (m, 2H), 0.90 (s, 9H), 0.09 (s, 6H).

C.ii. 6-[(R)-4-(tert-butyl-dimethyl-silanyloxy)-2-hydroxy-butylamino]-4H-benzo[1,4]thiazin-3-one:

A solution of 6-amino-4H-benzo[1,4]thiazin-3-one (10.68 g, 59.3 mmol; commercial) and (2R)-tert-butyl-dimethyl-(2-oxiranyl-ethoxy)-silane (first eluting compound of step C.i, 12.0 g, 59.3 mmol) in 9-1 EtOH/H$_2$O (320 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure to afford the title intermediate as a brown oil (18.8 g, 83% yield) which was used as such in the next step.

MS (ESI, m/z): 383.2 [M+H$^+$].

C.iii. 6-{(R)-5-[2-(tert-butyl-dimethyl-silanyloxy)-ethyl]-2-oxo-oxazolidin-3-yl}-4H-benzo[1,4]thiazin-3-one:

A solution of intermediate C.ii (23.5 g, 49.1 mmol) and CDI (9.57 g, 1.2 eq.) in THF (250 mL) was heated at 50° C. overnight. The mixture was concentrated under reduced pressure and partitioned between EA and water. The aq. layer was extracted once more with EA and the combined org. layers were dried over MgSO$_4$ and concentrated. The residue was purified by CC (DCM/MeOH/NH$_4$OH 1000:50:4) to afford the title intermediate as a colourless solid (8.4 g, 42% yield).

MS (ESI, m/z): 409.3 [M+H$^+$].

C.iv. 6-[(R)-5-(2-hydroxy-ethyl)-2-oxo-oxazolidin-3-yl]-4H-benzo[1,4]thiazin-3-one:

A solution of intermediate C.iii (8.4 g, 20.6 mmol) in THF (50 mL) was treated with TBAF (1M solution in THF, 24.7 mL, 1.2 eq) at 0° C. The solution was stirred at 0° C. for 6 h. The mixture was partitioned between water and EA and the aq. phase was extracted with EA (3×). The combined org. layers were washed with water and brine, dried over MgSO$_4$ and concentrated. The residue was triturated with Et$_2$O/EA to afford the title intermediate as an off-white solid (4.79 g, 79% yield).

MS (ESI, m/z): 295.5 [M+H$^+$].

C.v. Methanesulfonic acid 2-[(R)-2-oxo-3-(3-oxo-3,4-dihydro-2H-benzo[1,4]thiazin-6-yl)-oxazolidin-5-yl]-ethyl ester:

A solution of intermediate C.iv (4.7 g, 16.0 mmol) and DIPEA (7.54 mL, 2.9 eq.) in anhydrous DCM (80 mL) was cooled to 0° C. and treated dropwise with MsCl (1.50 mL, 1.2 eq.). The resulting mixture was stirred at 0° C. for 1 h. Water and DCM were added and the phases were separated. The org. layer was dried over MgSO$_4$ and concentrated under reduced pressure. The residue was purified by CC (DCM/MeOH/NH$_4$OH 1000:50:4) to afford the title intermediate as an off-white solid (5.80 g, 98% yield).

MS (ESI, m/z): 373.4 [M+H$^+$].

C.vi. 6-[(R)-5-(2-iodo-ethyl)-2-oxo-oxazolidin-3-yl]-4H-benzo[1,4]thiazin-3-one:

A suspension of intermediate C.v (3.5 g, 9.4 mmol) and NaI (4.23 g, 3 eq.) in 2-butanone (35 mL) was heated at 85° C. overnight. After cooling, the mixture was diluted with ether/EA (20 mL) and treated with 10% aq. Na$_2$S$_2$O$_3$ (60 mL). After stirring for 10 min, the phases were separated and the aq. layer was washed with EA. The combined org. layers were washed with water (2×), dried over MgSO$_4$ and concentrated under reduced pressure. The residue was triturated with Et$_2$O/EA to afford the title compound as an off-white solid (3.52 g, 93% yield).

MS (ESI, m/z): 405.0 [M+H$^+$].

Preparation D: (S)-3-(3-fluoro-4-methyl-phenyl)-5-iodomethyl-oxazolidin-2-one:

D.i. (S)-3-(3-fluoro-4-methyl-phenyl)-5-hydroxymethyl-oxazolidin-2-one:

A mixture of 3-fluoro-4-methyl-aniline (commercial; 1.25 g, 10 mmol), sat. aq. NaHCO$_3$ (10 mL) and acetone (10 mL) was treated dropwise with benzyl chloroformate (1.70 g, 1.41 mL, 1 eq.). After CO$_2$ evolution ceased, the mixture was partitioned between EA and sat. aq. NaHCO$_3$, the org. layer was dried over MgSO$_4$ and concentrated under reduced pressure. The resulting benzyl carbamate was dissolved in THF (50 mL) and cooled under argon to −78° C. n-BuLi (2.5M in hexanes, 6.45 mL, 1.1 eq.) was added dropwise, and the resulting solution was stirred for 1 h at that temperature. The reaction was then allowed to warm to −15° C. at which (S)-glycidyl butyrate (1.69 mL, 1.1 eq.) was added dropwise. The mixture was stirred at rt overnight. A tip of a spatula of Cs$_2$CO$_3$ was added, and the mixture was stirred at rt for 3 h. NH$_4$Cl and EA were added and the phases were separated. The aq. phase was extracted once more with EA and the combined org. extracts were washed several times with sat. aq. NH$_4$Cl, then with brine, dried over Na$_2$SO$_4$ and concentrated. The resulting orange solid was triturated with EA to afford the title intermediate as a pale yellow solid (1.18 g, 53% yield).

MS (ESI, m/z): 226.3 [M+H$^+$].

D.ii. Methanesulfonic acid (S)-3-(3-fluoro-4-methyl-phenyl)-2-oxo-oxazolidin-5-ylmethyl ester:

A solution of intermediate D.i (4.70 g, 20.9 mmol) in DCM (200 mL) was cooled to 0° C. DIPEA (9.9 mL, 2.9 eq) and MsCl (2.0 mL, 1.2 eq) were added and the mixture was stirred for 1 h at 0° C. The mixture was diluted with DCM and washed with water. The org. phase was dried over Mg SO$_4$ and concentrated. The residue was triturated with ether to give the title intermediate as a yellow solid (6.37 g, 100% yield).

$^1$H NMR (CDCl$_3$) δ: 7.36 (dd, J=11.7, 2.3 Hz, 1H), 7.13 (m, 2H), 4.91 (m, 1H), 4.46 (m, 2H), 4.13 (t, J=9.1 Hz, 1H), 3.92 (dd, J=9.1, 6.2 Hz, 1H), 3.10 (s, 3H), 2.25 (d, J=1.8 Hz, 3H).

MS (ESI, m/z): 330.3 [M+H$^+$].

D.iii. (S)-3-(3-fluoro-4-methyl-phenyl)-5-iodomethyl-oxazolidin-2-one:

A mixture of intermediate D.ii (6.30 g, 20.8 mmol) and NaI (12.5 g, 4 eq.) in acetone (100 mL) was heated at reflux for 3 h. The solvent was evaporated and the residue extracted with water/DCM. The org. layer was washed with brine, dried over MgSO$_4$ and concentrated under reduced pressure. The residue was triturated with ether/EA to afford the title compound as a slightly pink solid (6.3 g, 91% yield).

MS (ESI, m/z): 335.8 [M+H$^+$].

Preparation E: methanesulfonic acid (S)-2-oxo-3-(3-oxo-3,4-dihydro-2H-benzo[1,4]oxazin-6-yl)-oxazolidin-5-ylmethyl ester:

E.i. 6-[(S)-3-(tert-butyl-dimethyl-silanyloxy)-2-hydroxy-propylamino]-4H-benzo[1,4]oxazin-3-one:

To a solution of tert-butyl-dimethyl-((S)-1-oxiranyl-methoxy)-silane (commercial; 4.25 g, 22.6 mmol) in MeCN (70 mL) was added LiClO$_4$ (7.20 g, 3 eq.). 6-amino-4H-benzo[1,4]oxazin-3-one (commercial; 3.70 g, 1 eq.) was then added and the mixture was stirred at 50° C. for 6 h. The solvent was removed under reduced pressure and the residue was purified by CC (DCM/MeOH/NH$_4$OH 1000:25:2) to afford the title intermediate as a pale brown foam (5.25 g, 66% yield).

MS (ESI, m/z): 353.3 [M+H$^+$].

E.ii. 6-[(S)-5-(tert-butyl-dimethyl-silanylarymethyl)-2-oxo-oxazolidin-3-yl]-4H-benzo[1,4]oxazin-3-one:

A solution of intermediate E.i (10.24 g, 29 mmol) and CDI (9.71 g, 2 eq) in THF (140 mL) was heated at 50° C. for 2 h; the mixture was concentrated under reduced pressure and partitioned between EA and water. The org. layer was washed with water and brine, dried over MgSO$_4$, concentrated and triturated with Et$_2$O to afford the title intermediate as a pale yellow solid (6.30 g, 57% yield).

MS (ESI, m/z): 379.2 [M+H$^+$].

E.iii. 6-((S)-5-hydroxymethyl-2-oxo-oxazolidin-3-yl)-4H-benzo[1,4]oxazin-3-one:

A suspension of intermediate E.ii (6.30 g, 16.6 mmol) in THF (15 mL) was treated with TBAF (1M in THF, 16.6 mL) at 0° C. The solution was stirred at 0° C. for 3 h and then partitioned between water and EA. The aq. phase was extracted with EA (3×). The combined org. layers were washed with brine, dried over MgSO$_4$ and concentrated. The residue was triturated with EA afford the title intermediate as a colourless solid (3.49 g, 79% yield).

MS (ESI, m/z): 265.5 [M+H$^+$].

E.iv. Methanesulfonic acid (S)-2-oxo-3-(3-oxo-3,4-dihydro-2H-benzo[1,4]oxazin-6-yl)-oxazolidin-5-ylmethyl ester:

A suspension of intermediate E.iii (4.93 g, 18.7 mmol) in anhydrous DCM (110 mL) was treated with DIPEA (12.0 mL, 3.75 eq.) and the mixture was cooled to 0° C. Ms$_2$O (4.88 g, 1.5 eq.) was added portionwise. The resulting mixture was stirred at 0° C. for 15 min. Water was added and stirring was continued for 15 min at rt. The precipitated product was filtered, washed with water and DCM. The resulting solid was triturated with DCM/MeOH/NH$_4$OH (1000/25/2) to give the title compound as a colourless solid (3.785 g, 60% yield).

$^1$H NMR (DMSO-d6) δ: 10.72 (s, 1H), 7.29 (dd, J=2.1, 0.6 Hz, 1H), 6.94 (m, 2H), 4.95 (m, 1H), 4.52 (s, 2H), 4.49 (m, 2H), 4.11 (t, J=9.1 Hz, 1H), 3.73 (m, 2H), 3.23 (s, 3H).

MS (ESI, m/z): 343.3 [M+H$^+$].

Preparation F: 6-((R)-5-iodomethyl-2-oxo-oxazolidin-3-yl)-4H-benzo[1,4]thiazin-3-one:

F.i. 6-((R)-3-chloro-2-hydroxy-propylamino)-4H-benzo[1,4]thiazin-3-one:

A solution of 6-amino-4H-benzo[1,4]thiazin-3-one (18.39 g, 102 mmol; commercial) and (R)-epichlorohydrin (8.0 mL, 1 eq.) in 9-1 EtOH/H$_2$O (450 mL) was heated at 80° C. overnight. The mixture was concentrated under reduced pressure. Residual starting aniline could be removed by addition of Et$_2$O/EA followed by filtration. The filtrate containing the product was concentrated under reduced pressure to afford the title intermediate as a beige solid (22.52 g, 81% yield) which was used as such in the next step.

MS (ESI, m/z): 273.2 [M+H$^+$].

F.ii. 64(R)-5-chloromethyl-2-oxo-oxazolidin-3-yl)-4H-benzo[1,4]thiazin-3-one:

A solution of intermediate F.i (22.0 g, 81.0 mmol) and CDI (15.7 g, 1.2 eq.) in THF (500 mL) was heated at 50° C. overnight. The mixture was concentrated under reduced pressure and partitioned between DCM and water. The aq. layer was extracted once more with DCM and the combined org. layers were washed with 0.5M HCl (2×) and water, dried over MgSO$_4$ and concentrated. The residue was triturated with DCM/MeOH to afford the title intermediate as a yellow solid (8.79 g, 36% yield).

MS (ESI, m/z): 299.1 [M+H$^+$].

F.iii. 6-((R)-5-iodomethyl-2-oxo-oxazolidin-3-yl)-4H-benzo[1,4]thiazin-3-one:

A mixture of intermediate F.ii (8.75 g, 29 mmol) and NaI (13.17 g, 3 eq) in 2-butanone (75 mL) was heated at 85° C. for 4 days. After cooling to rt, the mixture was diluted with 10% aq. Na$_2$S$_2$O$_3$ (150 mL) and ether/EA (75 mL). The mixture was vigorously stirred for 10 min and filtered. The solids were thoroughly washed with water and ether and dried under HV to afford an off-white solid (9.27 g, 81% yield).

$^1$H NMR (DMSO-d6) δ: 10.56 (s, 1H), 7.31 (m, 2H), 7.12 (dd, J=8.5, 2.3 Hz, 1H), 4.71 (m, 1H), 4.14 (t, J=9.1 Hz, 1H), 3.59 (m, 3H), 3.31 (s, 2H). MS (ESI, m/z): 390.9 [M+H$^+$].

Preparation G: 6-[(S)-5-(2-iodo-ethyl)-2-oxo-oxazolidin-3-yl]-4H-benzo[1,4]thiazin-3-one:

G.i. Toluene-4-sulfonic acid (S)-4-(tert-butyl-dimethyl-silanyloxy)-2-hydroxy-butyl ester:

To a solution of (2S)-4-(tert-butyl-dimethyl-silanyloxy)-butane-1,2-diol (23.9 g, 108 mmol; second eluting compound in Preparation C, step C.i) and DMAP (2.65 g, 0.2 eq) in DCM (80 mL) cooled to 0° C. were added TEA (43.8 mL, 2.9 eq.) and a solution of TsCl (20.7 g, 1.1 eq.) in DCM (15 mL). The mixture was stirred at rt for 5 h, poured on sat. aq. NaHCO$_3$ and extracted with DCM. The org. layer was dried over MgSO$_4$ and concentrated. The residue was purified by CC (Hept/EA 2:1) to afford the title intermediate as a colourless oil (31.3 g, 77% yield).

$^1$H NMR (CDCl$_3$) δ: 7.80 (d, J=7.6 Hz, 2H), 7.34 (d, J=7.6 Hz, 2H), 4.02 (m, 3H), 3.80 (m, 2H), 2.45 (s, 3H), 1.70 (m, 2H), 1.27 (m, 1H), 0.87 (s, 9H), 0.05 (s, 6H).

G.ii. (2S)-tert-butyl-dimethyl-(2-oxiranyl-ethoxy)-silane:

To a solution of intermediate G.i (31.1 g, 83.1 mmol) in THF (350 mL) was added 2M NaOH (35 mL) and the mixture was vigorously stirred at rt for 3 h. The mixture was taken in 1M NaOH (200 mL) and extracted with TBME (2×). The combined org. layers were washed with water and brine, dried over MgSO$_4$ and concentrated. The resulting oil was purified by Kugelrohr-distillation (ca. 70° C. at 0.1 mbar) to afford the title intermediate as a colourless oil (14.7 g, 87% yield).

$^1$H NMR (CDCl$_3$) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).

G.iii. 6-[(S)-4-(tert-butyl-dimethyl-silanyloxy)-2-hydroxy-butylamino]-4H-benzo[1,4]thiazin-3-one:

A solution of 6-amino-4H-benzo[1,4]thiazin-3-one (8.0 g, 44.5 mmol; commercial) and intermediate G.ii (9.0 g, 1 eq.) in 9-1 EtOH/H$_2$O (250 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure to afford the title intermediate as a brown oil (14.58 g, 86% yield) which was used as such in the next step.

MS (ESI, m/z): 383.2 [M+H$^+$].

G.iv. 6-{(S)-5-[2-(tert-butyl-dimethyl-silanyloxy)-ethyl]-2-oxo-oxazolidin-3-yl}-4H-benzo[1,4]thiazin-3-one:

A solution of intermediate G.iii (14.5 g, 37.9 mmol) and CDI (8.60 g, 1.4 eq.) in THF (180 mL) was heated at 50° C. overnight. The mixture was concentrated under reduced pressure and partitioned between EA and water. The aq. layer was extracted once more with EA and the combined org. layers were dried over MgSO$_4$ and concentrated. The residue was purified by CC (DCM/MeOH/NH$_4$OH 1000:50:4) to afford the title intermediate as a colourless solid (5.56 g, 36% yield).

MS (ESI, m/z): 409.3 [M+H$^+$].

G.v. 6-[(S)-5-(2-hydroxy-ethyl)-2-oxo-oxazolidin-3-yl]-4H-benzo[1,4]thiazin-3-one:

A solution of intermediate G.iv (5.50 g, 13.6 mmol) in THF (30 mL) was treated with TBAF (1M solution in THF, 16.3 mL, 1.2 eq.) at 0° C. The solution was stirred at 0° C. for 6 h. The mixture was partitioned between water and EA and the aq. phase was extracted with EA (3×). The combined org. layers were washed with water (3×) and brine, dried over MgSO$_4$ and concentrated. The residue was triturated with Et$_2$O/EA to afford the title intermediate as an off-white solid (3.08 g, 77% yield).

MS (ESI, m/z): 295.5 [M+H$^+$].

G.vi. Methanesulfonic acid 2-[(S)-2-oxo-3-(3-oxo-3,4-dihydro-2H-benzo[1,4]thiazin-6-yl)-oxazolidin-5-yl]-ethyl ester:

A solution of intermediate G.v (3.0 g, 10.2 mmol) and DIPEA (4.8 mL, 2.9 eq.) in anhydrous DCM (50 mL) was cooled to 0° C. and treated dropwise with MsCl (0.96 mL, 1.2 eq.). The resulting mixture was stirred at 0° C. for 1 h. Water and DCM were added and the phases separated. The org. layer was dried over MgSO$_4$ and concentrated under reduced pressure. The residue was triturated with ether to afford the title intermediate as an off-white solid (3.64 g, 96% yield).

MS (ESI, m/z): 373.4 [M+H$^+$].

G.vii. 6-[(S)-5-(2-iodo-ethyl)-2-oxo-oxazolidin-3-yl]-4H-benzo[1,4]thiazin-3-one:

A suspension of intermediate G.vi (2.5 g, 6.7 mmol) and NaI (3.02 g, 3 eq.) in 2-butanone (25 mL) was heated at 85° C. overnight. After cooling, the mixture was diluted with ether/EA (20 mL) and treated with 10% aq. Na$_2$S$_2$O$_3$ (60 mL). After stirring for 10 min the phases were separated and the aq. layer was washed with EA. The combined org. layers were washed with water (2×), dried over MgSO$_4$ and concentrated under reduced pressure. The residue was triturated with Et$_2$O/EA to afford the title intermediate as a slightly orange solid (2.11 g, 78% yield).

$^1$H NMR (DMSO-d6) δ: 10.55 (s, 1H), 7.30 (m, 2H), 7.04 (dd, J=8.5, 2.3 Hz, 1H), 4.68 (m, 1H), 4.10 (t, J=8.8 Hz, 1H), 3.70 (dd, J=8.8, 6.7 Hz, 1H), 3.41 (s, 2H), 3.29 (m, 2H), 2.23 (m, 2H).

MS (ESI, m/z): 405.1 [M+H$^+$].

Example 1

6-{(R)-5-[3-hydroxy-3-(7-methoxy-2-oxo-2H-quinolin-1-ylmethyl)azetidin-1-ylmethyl]-2-oxo-oxazolidin-3-yl}-4H-benzo[1,4]thiazin-3-one 1.i. 3-hydroxy-3-(7-methoxy-2-oxo-2H-quinolin-1-ylmethyl)-azetidine-1-carboxylic acid tert-butyl ester:

A solution of oxa-5-azaspiro[2.3]hexane-5-carboxylic acid tert-butyl ester (69 mg; prepared according to WO 2007/044515) in DMF (1 mL) was added to a suspension of 7-methoxy-2(1H)-quinolinone (60 mg; commercial) and Cs$_2$CO$_3$ (223 mg, 2 eq.) in DMF (2 mL). The reaction mixture was stirred at 80° C. for 10 days. The solvent was removed under reduced pressure and the residue was partitioned between water and EA. The aq. layer was extracted with EA. The combined org. layers were dried over Na$_2$SO$_4$, filtered, evaporated and purified by CC (DCM-MeOH 19:1 to 9:1) to afford the title intermediate as a yellow oil (12 mg, 10% yield).

MS (ESI, m/z): 361.3 [M+H$^+$].

1.ii. 1-(3-hydroxy-azetidin-3-ylmethyl)-7-methoxy-1H-quinolin-2-one:

Starting from intermediate 1.i (12 mg) and using procedure A, the title intermediate was obtained as a yellow oil (8 mg, 92% yield).

$^1$H NMR (DMSO-d6) δ: 7.61 (d, J=9.4 Hz, 1H), 7.39 (m, 2H), 6.81 (dd, J=8.5, 1.5 Hz, 1H), 6.48 (d, J=9.4 Hz, 1H), 4.65 (s, 2H), 3.86 (s, 4H).

1.iii. 6-{(R)-5-[3-hydroxy-3-(7-methoxy-2-oxo-2H-quinolin-1-ylmethyl)-azetidin-1-ylmethyl]-2-oxo-oxazolidin-3-yl}-4H-benzo[1,4]thiazin-3-one:

Starting from intermediate 1.ii (8 mg) and the compound of Preparation A, and using procedure B, the title compound was obtained as a colourless solid (4 mg, 22% yield).

$^1$H NMR (CDCl$_3$) δ: 7.86 (s, 1H), 7.71 (d, J=9.4 Hz, 1H), 7.53 (d, J=8.5 Hz, 1H), 7.42 (m, 2H), 7.29 (d, J=8.5 Hz, 1H), 6.97 (dd, J=8.8, 2.3 Hz, 1H), 6.89 (dd, J=8.5, 1.8 Hz, 1H), 6.60 (d, J=9.4 Hz, 1H), 6.31 (s, 1H), 4.65 (m, 3H), 4.08 (t, J=8.8 Hz, 1H), 3.87 (m, 4H), 3.58 (m, 3H), 3.41 (s, 2H), 3.08 (m, 2H), 2.87 (dd, J=5.9, 3.5 Hz, 2H).

MS (ESI, m/z): 522.9 [M+H$^+$].

Example 2

6-{(R)-5-[3-(7-methoxy-2-oxo-2H-quinolin-1-ylmethyl)-azetidin-1-ylmethyl]-2-oxo-oxazolidin-3-yl}-4H-benzo[1,4]thiazin-3-one 2.i. 3-(7-methoxy-2-oxo-2H-quinolin-1-ylmethyl)-azetidine-1-carboxylic acid tert-butyl ester:

A suspension of 7-methoxy-2(1H)-quinolinone (405 mg; commercial) in DMF (10 mL) was treated with NaH (111 mg; 50% dispersion in oil). The mixture was stirred at rt for 30 min before the addition of a solution of 3-[[(methylsulfonyl)oxy]methyl]-1-azetidinecarboxylic acid tert-butyl ester (674 mg; prepared according to WO 02/066470) in DMF (2 mL). The mixture was heated at 100° C. overnight. The reaction mixture was partitioned between EA and water. The org. phase was dried over MgSO$_4$, concentrated under reduced pressure and purified by CC (Hept/EA 2:1 to 0:1). The second eluting compound was isolated as a colourless foam (350 mg, 44% yield).

$^1$H NMR (CDCl$_3$) δ: 7.59 (d, J=9.4 Hz, 1H), 7.48 (d, J=8.5 Hz, 1H), 6.83 (dd, J=8.5, 2.3 Hz, 1H), 6.76 (d, J=2.3 Hz, 1H), 6.52 (d, J=9.4 Hz, 1H), 4.5 (br., 2H), 3.95 (m, 4H), 3.91 (s, 3H), 3.04 (m, 1H), 1.42 (s, 9H).

MS (ESI, m/z): 345.2 [M+H$^+$].

2.ii. 3-(7-methoxy-2-oxo-2H-quinolin-1-ylmethyl)-azetidine:

Starting from intermediate 2.i (350 mg) and using procedure A, the title intermediate was obtained as a yellowish foam (200 mg, 80% yield).

$^1$H NMR (CDCl$_3$) δ: 7.58 (d, J=9.4 Hz, 1H), 7.45 (d, J=9.1 Hz, 1H), 6.81 (m, 2H), 6.52 (d, J=9.4 Hz, 1H), 4.51 (d, J=7.0 Hz, 2H), 3.91 (s, 3H), 3.60 (m, 4H), 2.27 (m, 1H).

2.iii. 6-{(R)-5-[3-(7-methary-2-oxo-2H-quinolin-1-ylmethyl)-azetidin-1-ylmethyl]-2-oxo-oxazolidin-3-yl}-4H-benzo[1,4]thiazin-3-one:

Starting from intermediate 2.ii (65 mg) and the compound of Preparation A, and using procedure B, the title compound was obtained as a beige foam (28 mg, 21% yield).

MS (ESI, m/z): 507.0 [M+H$^+$].

Example 3

1-{1-[(R)-3-(2,3-dihydro-benzo[1,4]dioxin-6-yl)-2-oxo-oxazolidin-5-ylmethyl]-azetidin-3-ylmethyl}-7-methoxy-1H-quinolin-2-one Starting from intermediate 2.ii (65 mg) and the compound of Preparation B (106 mg), and using procedure B, the title compound was obtained as a beige foam (30 mg, 23% yield).

$^1$H NMR (CDCl$_3$) δ: 7.59 (d, J=9.4 Hz, 1H), 7.46 (d, J=9.1 Hz, 1H), 7.08 (d, J=2.6 Hz, 1H), 7.00 (m, 1H), 6.83 (m, 3H), 6.52 (d, J=9.4 Hz, 1H), 4.47 (dd, J=6.7, 1.8 Hz, 2H), 4.24 (s, 4H), 3.92 (m, 3H), 3.81 (m, 1H), 3.25 (m, 2H), 2.77 (s, 2H). MS (ESI, m/z): 478.0 [M+H$^+$].

Example 4

6-{(R)-5-[3-(7-methoxy-2-oxo-2H-quinoxalin-1-ylmethyl)-azetidin-1-ylmethyl]-2-oxo-oxazolidin-3-yl}-4H-benzo[1,4]thiazin-3-one 4.i. 3-(7-methoxy-2-oxo-2H-quinoxalin-1-ylmethyl)-azetidine-1-carboxylic acid tert-butyl ester:

Using the procedure of Example 2, step 2.i, but starting from 7-methoxy-2(1H)-quinoxalinone (1.00 g; prepared according to WO 2006/134378) and 3-[[(methylsulfonyl)oxy]methyl]-1-azetidinecarboxylic acid tert-butyl ester (1.65 g; prepared according to WO 02/066470), the second eluting compound was isolated as a yellow oil (700 mg, 35% yield).
MS (ESI, m/z): 346.2 [M+H$^+$].

4.ii. 3-(7-methoxy-2-oxo-2H-quinoxalin-1-ylmethyl)-azetidine:

Starting from intermediate 4.i (700 mg) and using procedure A, the title intermediate was obtained as an orange foam (400 mg, 80% yield).
MS (ESI, m/z): 246.4 [M+H$^+$].

4.iii. 6-{(R)-[3-(7-methary-2-oxo-2H-quinoxalin-1-ylmethyl)-azetidin-1-ylmethyl]-2-oxo-oxazolidin-3-yl}-4H-benzo[1,4]thiazin-3-one:

Starting from intermediate 4.ii (90 mg) and the compound of Preparation A (157 mg) and using procedure B, the title compound was obtained as a brown solid (20 mg, 11% yield).
$^1$H NMR (DMSO-d6) δ: 10.54 (d, J=0.6 Hz, 1H), 8.03 (s, 1H), 7.73 (d, J=9.7 Hz, 1H), 7.30 (m, 2H), 6.98 (m, 2H), 4.41 (d, J=6.4 Hz, 2H), 3.99 (d, J=0.6 Hz, 2H), 3.89 (s, 3H), 3.68 (m, 1H), 3.42 (s, 2H), 3.06 (m, 2H), 2.68 (m, 2H).
MS (ESI, m/z): 508.2 [M+H$^+$].

Example 5

6-((R)-5-{2-[3-(7-methoxy-2-oxo-2H-quinolin-1-ylmethyl)-azetidin-1-yl]-ethyl}-2-oxo-oxazolidin-3-yl)-4H-benzo[1,4]thiazin-3-one Starting from intermediate 2.ii (65 mg) and the compound of Preparation C (118 mg), and using procedure B, the title compound was obtained as a beige foam (47 mg, 34% yield).
MS (ESI, m/z): 521.4 [M+H$^+$].

Example 6

6-((R)-5-{2-[3-(7-methoxy-2-oxo-2H-quinoxalin-1-ylmethyl)-azetidin-1-yl]-ethyl}-2-oxo-oxazolidin-3-yl)-4H-benzo[1,4]thiazin-3-one Starting from intermediate 4.ii (90 mg) and the compound of Preparation C (148 mg) and using procedure B, the title compound was obtained as beige foam (54 mg, 28% yield).
MS (ESI, m/z): 522.3 [M+H$^+$].

Example 7

6-{(R)-5-[4-(7-methoxy-2-oxo-2H-quinolin-1-ylmethyl)-piperidin-1-ylmethyl]-2-oxo-oxazolidin-3-yl}-4H-benzo[1,4]thiazin-3-one 7.i. 4-(7-methoxy-2-oxo-2H-quinolin-1-ylmethyl)-piperidine-1-carboxylic acid tert-butyl ester:

Using the procedure of Example 2, step 2.i, but starting from 7-methoxy-2(1H)-quinolinone (350 mg; commercial) and 4-[[(methylsulfonyl)oxy]methyl]-1-piperidinecarboxylic acid tert-butyl ester (645 mg; commercial), the second eluting compound was isolated as a colourless foam (227 mg; 30% yield).
MS (ESI, m/z): 373.3 [M+H$^+$].

7.ii. 4-(7-methoxy-2-oxo-2H-quinolin-1-ylmethyl)-piperidine:

Starting from intermediate 7.i (327 mg) and using procedure A, the title intermediate was obtained as a colourless foam (210 mg, 88% yield).
$^1$H NMR (CDCl$_3$) δ: 7.59 (d, J=9.4 Hz, 1H), 7.47 (m, 1H), 6.82 (m, 2H), 6.53 (d, J=9.4 Hz, 1H), 4.18 (m, 2H), 3.91 (s, 3H), 3.10 (m, 2H), 2.55 (td, J=12.3, 2.6 Hz, 2H), 2.06 (s, 2H), 1.67 (m, 2H), 1.42 (m, 2H).

7.iii. 6-{(R)-5-[4-(7-methary-2-oxo-2H-quinolin-1-ylmethyl)-piperidin-1-ylmethyl]-2-oxo-oxazolidin-3-yl}-4H-benzo[1,4]thiazin-3-one:

Starting from intermediate 7.ii (70 mg) and the compound of Preparation A (110 mg), and using procedure B, the title compound was obtained as a yellowish foam (53 mg, 38% yield).
$^1$H NMR (DMSO-d6) δ: 10.53 (s, 1H), 7.80 (d, J=9.4 Hz, 1H), 7.63 (d, J=8.8 Hz, 1H), 7.30 (m, 2H), 7.12 (m, 1H), 6.90 (m, 2H), 6.40 (d, J=9.4 Hz, 1H), 4.15 (m, 2H), 4.02 (m, 1H), 3.87 (s, 3H), 3.43 (s, 2H), 2.60 (m, 2H), 1.99 (m, 2H), 1.50 (m, 2H), 1.35 (m, 2H). MS (ESI, m/z): 535.5 [M+H$^+$].

Example 8

1-{1-[(R)-3-(2,3-dihydro-benzo[1,4]dioxin-6-yl)-2-oxo-oxazolidin-5-ylmethyl]-piperidin-4-ylmethyl}-7-methoxy-1H-quinolin-2-one Starting from intermediate 7.ii (70 mg) and the compound of Preparation B (102 mg), and using procedure B, the title compound was obtained as a yellowish foam (48 mg, 37% yield).
$^1$H NMR (DMSO-d6) δ: 7.79 (d, J=9.4 Hz, 1H), 7.63 (d, J=8.5 Hz, 1H), 7.10 (d, J=2.6 Hz, 1H), 6.88 (m, 4H), 6.40 (d, J=9.4 Hz, 1H), 4.21 (m, 6H), 4.03 (d, J=1.8 Hz, 2H), 3.87 (s, 3H), 2.60 (m, 2H), 1.98 (s, 3H), 1.50 (m, 2H), 1.35 (m, 2H).
MS (ESI, m/z): 506.3 [M+H$^+$].

Example 9

1-{1-[(R)-3-(3-fluoro-4-methyl-phenyl)-2-oxo-oxazolidin-5-ylmethyl]-piperidin-4-ylmethyl}-7-methoxy-1H-quinolin-2-one Starting from intermediate 7.ii (70 mg) and the compound of Preparation D (94 mg), and using procedure B, the title compound was obtained as a yellowish foam (30 mg, 24% yield).
MS (ESI, m/z): 480.3 [M+H$^+$].

Example 10

6-{(R)-5-[3-(7-methoxy-2-oxo-3,4-dihydro-2H-quinolin-1-ylmethyl)azetidin-1-ylmethyl]-2-oxo-oxazolidin-3-yl}-4H-benzo[1,4]thiazin-3-one 10.i. 3-(7-methoxy-2-oxo-3,4-dihydro-2H-quinolin-1-ylmethyl)-azetidine-1-carboxylic acid tert-butyl ester:

Using the procedure of Example 2, step 2.i, but starting from 3,4-dihydro-7-methoxy-2(1H)-quinolinone (prepared according to WO 2006/134378; 886 mg) and 3-[[(methylsulfonyl)oxy]methyl]-1-azetidinecarboxylic acid tert-butyl ester (1459 mg; prepared according to WO 02/066470), the title compound was isolated as a colourless oil (1223 mg; 71% yield).

$^1$H NMR (DMSO-d6) δ: 7.07 (dd, J=7.9, 0.6 Hz, 1H), 6.54 (m, 2H), 4.18 (d, J=7.3 Hz, 2H), 3.94 (t, J=8.5 Hz, 2H), 3.77 (m, 5H), 2.81 (m, 2H), 2.62 (m, 2H), 1.43 (s, 9H). MS (ESI, m/z): 347.2 [M+H$^+$].

10.ii. 3-(7-methoxy-2-oxo-3,4-dihydro-2H-quinolin-1-ylmethyl)-azetidine:

Starting from intermediate 10.i (1223 mg) and using procedure A, the title intermediate was obtained as a colourless oil (565 mg, 65% yield).

MS (ESI, m/z): 247.5 [M+H$^+$].

10.iii. 6-{(R)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]thiazin-3-one:

Starting from intermediate 10.ii (110 mg) and the compound of Preparation A (191 mg), and using procedure B, the title compound was obtained as a yellowish foam (74 mg, 32% yield).

MS (ESI, m/z): 509.1 [M+H$^+$].

Example 11

6-{(S)-5-[3-(7-methoxy-2-oxo-3,4-dihydro-2H-quinolin-1-ylmethyl)azetidin-1-ylmethyl]-2-oxo-oxazolidin-3-yl}-4H-benzo[1,4]thiazin-3-one Starting from intermediate 10.ii (110 mg) and the compound of Preparation F (191 mg) and using procedure B, the title compound was obtained as a yellowish foam (75 mg, 33% yield).

$^1$H NMR (DMSO-d6) δ: 10.53 (s, 1H), 7.30 (m, 2H), 7.09 (m, 2H), 6.62 (d, J=2.3 Hz, 1H), 6.56 (dd, J=8.2, 2.3 Hz, 1H), 4.61 (s, 1H), 4.02 (m, 3H), 3.72 (m, 3H), 3.42 (s, 2H), 3.29 (m, 7H), 2.95 (m, 2H), 2.70 (m, 5H).

MS (ESI, m/z): 509.1 [M+H$^+$].

Example 12

6-{(R)-5-[3-(7-methoxy-2-oxo-3,4-dihydro-2H-quinolin-1-ylmethyl)azetidin-1-ylmethyl]-2-oxo-oxazolidin-3-yl}-4H-benzo[1,4]oxazin-3-one Starting from intermediate 10.ii (110 mg) and the compound of Preparation E (160 mg), and using procedure C, the title compound was obtained as a yellowish foam (50 mg, 23% yield).

MS (ESI, m/z): 493.1 [M+H$^+$].

Example 13

6-{(R)-5-[3-(7-methoxy-2-oxo-2H-quinoxalin-1-ylmethyl)-azetidin-1-ylmethyl]-2-oxo-oxazolidin-3-yl}-4H-benzo[1,4]oxazin-3-one Starting from intermediate 4.ii (90 mg) and the compound of Preparation E (125 mg) and using procedure C, the title compound was obtained as a brown solid (20 mg, 11% yield).

MS (ESI, m/z): 492.2 [M+H$^+$].

Example 14

1-{1-[(R)-3-(2,3-dihydro-benzo[1,4]dioxin-6-yl)-2-oxo-oxazolidin-5-ylmethyl]-azetidin-3-ylmethyl}-7-methoxy-1H-quinoxalin-2-one Starting from intermediate 4.ii (90 mg) and the compound of Preparation B (135 mg) and using procedure B, the title compound was obtained as a brown foam (22 mg, 12% yield). MS (ESI, m/z): 479.3 [M+H$^+$].

Example 15

6-methoxy-4-[1-{(R)-2-oxo-3-(3-oxo-3,4-dihydro-2H-benzo[1,4]thiazin-6-yl)-oxazolidin-5-ylmethyl]-piperidin-4-yl}-4H-pyrido[2,3-b]pyrazin-3-one 15.i. 4-(6-methoxy-3-nitro-pyridin-2-ylamino)-piperidine-1-carboxylic acid tert-butyl ester:

A mixture of 4-amino-1-Boc-piperidine (commercial; 6.7 g, 35 mmol), 2-chloro-6-methoxy-3-nitro-pyridine (1 eq.) and K$_2$CO$_3$ (1 eq.) in MeCN (100 mL) and DMF (30 mL) was heated at 60° C. for 3 h. The mixture was filtered and concentrated in vacuo. The residue was taken up in ether/water 1:1, the org. phase dried over MgSO$_4$ and concentrated. The residue was triturated with EA and filtered to afford 4.5 g of pure product. The filtrate was concentrated and purified by CC (Hept/EA 9:1, 4:1, 2:1) to give another 4 g of product. In total 8.5 g (70% yield) of a yellow solid were obtained.

$^1$H NMR (CDCl$_3$) δ: 8.62 (m, 1H), 8.31 (d, J=9.4 Hz, 1H), 6.07 (d, J=9.1 Hz, 1H), 4.32 (m, 1H), 4.05 (m, 2H), 3.95 (s, 3H), 3.02 (s, 2H), 2.10 (m, 2H), 1.60 (s, 3H), 1.47 (m, 9H).

15.ii. 4-(3-amino-6-methoxy-pyridin-2-ylamino)-piperidine-1-carboxylic acid tert-butyl ester:

A solution of intermediate 15.i (8.45 g) in EtOH/EA (1:1; 300 mL) was hydrogenated over 10% Pd/C for 4 h. The catalyst was filtered off, the filtrate was evaporated under reduced pressure and the residue was purified by CC (Hept/EA 1:2), affording a purple solid (5.4 g, 70% yield).

MS (ESI, m/z): 323.3 [M+H$^+$].

15.iii. 4-[3-(ethoxycarbonylmethyl-amino)-6-methoxy-pyridin-2-ylamino]-piperidine-1-carboxylic acid tert-butyl ester:

A suspension of intermediate 15.ii (5.38 g), ethyl bromoacetate (2.9 g), K$_2$CO$_3$ (4.6 g) in DMF/MeCN (1:2, 120 mL) was stirred at rt overnight. The reaction mixture was filtered and the filtrate was evaporated under reduced pressure. The residue was dissolved in EA/MeOH (19:1, 200 mL) and washed with water. The org. phase was dried over MgSO$_4$, filtered, concentrated under reduced pressure and purified by CC (Hept/EA; 2:1 then 1:1) affording a dark oil (5.29 g; 77% yield).

MS (ESI, m/z): 409.4 [M+H$^+$].

15.iv. 4-(6-methoxy-3-oxo-3H-pyrido[2,3-b]pyrazin-4-yl)-piperidine-1-carboxylic acid tert-butyl ester:

A solution of intermediate 15.iii (5.26 g) in toluene (240 mL) was treated with AcOH (1 mL) and the mixture was refluxed overnight under N$_2$. The reaction mixture was concentrated under reduced pressure and the residue was dissolved in DCM (200 mL) and treated with MnO$_2$ (21.2 g) at rt for 6 h. The reaction mixture was filtered and the filtrate was evaporated under reduced pressure and purified by CC (Hept/EA, 2:1 then 1:1), affording a beige solid (2.3 g, 49% yield).

$^1$H NMR (DMSO-d6) δ: 8.11 (d, J=8.5 Hz, 1H), 8.07 (s, 1H), 6.83 (d, J=8.5 Hz, 1H), 5.42 (m, 1H), 4.11 (m, 2H), 3.93 (s, 3H), 2.77 (m, 4H), 1.63 (m, 2H), 1.40 (s, 9H). MS (ESI, m/z): 361.4 [M+H$^+$].

15.v. 6-methoxy-4-piperidin-4-yl-4H-pyrido[2,3-b]pyrazin-3-one:

Starting from intermediate 15.iv (2.30 g) and using procedure A, the title intermediate was obtained as a yellow solid (223 mg, 13% yield) after CC (DCM/MeOH 19:1, then 9:1+ 1% NH$_4$OH).

MS (ESI, m/z): 261.2 [M+H$^+$].

15.vi. 6-methoxy-4-{1-[(R)-2-oxo-3-(3-oxo-3,4-dihydro-2H-benzo[1,4]thiazin-6-yl)-oxazolidin-5-ylmethyl]-piperidin-4-yl}-4H-pyrido[2,3-b]pyrazin-3-one:

Starting from intermediate 15.v (101 mg) and the compound of Preparation A (167 mg) and using procedure B, the title compound was obtained as a beige solid (71 mg, 35% yield).

$^1$H NMR (DMSO-d6) δ: 10.57 (d, J=0.6 Hz, 1H), 8.11 (d, J=8.5 Hz, 1H), 8.05 (s, 1H), 7.33 (m, 2H), 7.14 (m, H), 6.83 (d, J=8.5 Hz, 1H), 4.85 (m, 1H), 4.03 (s, 1H), 3.91 (s, 3H), 3.76 (m, 1H), 3.44 (s, 3H), 3.08 (m, 2H), 2.93 (m, 2H), 2.73 (m, 2H), 2.27 (m, 2H), 1.16 (m, 2H).

MS (ESI, m/z): 523.1 [M+H$^+$].

Example 16

6-methoxy-4-{1-[(R)-2-oxo-3-(3-oxo-3,4-dihydro-2H-benzo[1,4]oxazin-6-yl)-oxazolidin-5-ylmethyl]-piperidin-4-yl}-4H-pyrido[2,3-b]pyrazin-3-one Starting from intermediate 15.v (100 mg) and the compound of Preparation E (145 mg) and using procedure C, the title compound was obtained as a beige solid (64 mg, 32% yield).

$^1$H NMR (DMSO-d6) δ: 10.72 (s, 1H), 8.11 (d, J=8.5 Hz, 1H), 8.05 (s, 1H), 7.33 (t, J=1.5 Hz, 1H), 6.97 (d, J=1.5 Hz, 2H), 6.83 (d, J=8.5 Hz, 1H), 5.25 (m, 1H), 4.83 (m, 1H), 4.54 (m, 2H), 4.05 (m, 1H), 3.92 (s, 3H), 3.75 (m, 1H), 3.07 (m, 2H), 2.92 (m, 2H), 2.72 (d, J=5.6 Hz, 2H), 2.27 (m, 2H), 1.59 (m, 2H).

MS (ESI, m/z): 507.2 [M+H$^+$].

Example 17

6-{(R)-5-[(R)-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one 17.i. (S)-3-(7-methoxy-2-oxo-2H-quinolin-1-ylmethyl)-pyrrolidine-1-carboxylic acid tert-butyl ester:

Using the procedure of Example 2, step 2.i, but starting from 7-methoxy-2(1H)-quinolinone (prepared according to WO 2006/134378; 500 mg) and 3-[[(methylsulfonyl)oxy]methyl]-1-pyrrolidinecarboxylic acid tert-butyl ester (797 mg; prepared according to *J. Med. Chem.* (1999), 42, 677-690), the second eluting compound was isolated as a colourless oil (240 mg; 23% yield).

$^1$H NMR (CDCl$_3$) δ: 7.60 (d, J=9.4 Hz, 1H), 7.48 (d, J=8.8 Hz, 1H), 6.81 (m, 2H), 6.53 (d, J=9.4 Hz, 1H), 3.91 (m, 3H), 3.52 (m, 2H), 3.35 (m, 2H), 2.76 (m, 1H), 1.89 (m, 4H), 1.45 (m, 9H).

17.ii. (S)-7-methoxy-1-pyrrolidin-3-ylmethyl-1H-quinolin-2-one:

Starting from intermediate 17.i (220 mg) and using procedure A, the title intermediate was obtained as a colourless oil (120 mg, 75% yield).

$^1$H NMR (CDCl$_3$) δ: 7.62 (d, J=9.4 Hz, 1H), 7.49 (d, J=8.8 Hz, 1H), 6.84 (m, 2H), 6.53 (d, J=9.4 Hz, 1H), 4.41 (m, 2H), 4.19 (m, 1H), 3.92 (s, 3H), 3.48 (s, 1H), 3.28 (m, 1H), 3.02 (m, 3H), 2.80 (m, 1H), 2.01 (m, 1H), 1.78 (m, 1H).

17.iii. 6-{(R)-5-[(R)-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one:

Starting from intermediate 17.ii (100 mg) and the compound of Preparation A (151 mg) and using procedure B, the title compound was obtained as a beige solid (8 mg, 4% yield).

MS (ESI, m/z): 521.2 [M+H$^+$].

Example 18

6-{(R)-5-[(RS)-3-hydroxy-3-(7-methoxy-2-oxo-2H-quinolin-1-ylmethyl)pyrrolidin-1-ylmethyl]-2-oxo-oxazolidin-3-yl}-4H-benzo[1,4]thiazin-3-one 18.i. rac-3-hydroxy-3-(7-methoxy-2-oxo-2H-quinolin-1-ylmethyl)-pyrrolidine-1-carboxylic acid tert-butyl ester:

A solution of 7-methoxy-1H-quinolin-2-one (650 mg, 3.7 mmol) and 1-oxa-5-aza-spiro[2.4]heptane-5-carboxylic acid tert-butyl ester (1 eq., commercial) in DMF (10 mL) was treated with Cs$_2$CO$_3$ (1 eq.) and heated at 70° C. overnight. The mixture was partitioned between EA and water, the org. phase washed with water and brine, dried over MgSO$_4$ and concentrated. The product was purified by CC (EA/Hept 1:1, EA) to give the desired intermediate as a yellowish oil (650 mg, 47% yield).

$^1$H NMR (CDCl$_3$) δ: 7.70 (d, J=9.4 Hz, 1H), 7.52 (d, J=8.5 Hz, 1H), 6.87 (m, 2H), 6.60 (d, J=9.4 Hz, 1H), 4.59 (m, 1H), 4.45 (m, 1H), 3.89 (s, 3H), 3.49 (m, 6H), 1.40 (br. s, 9H).

18.ii. rac-1-(3-hydroxy-pyrrolidin-3-ylmethyl)-7-methoxy-1H-quinolin-2-one:

Starting from intermediate 18.i (600 mg) and using procedure A, the title intermediate was obtained as a colourless oil (440 mg, 100% yield).

$^1$H NMR (CDCl$_3$) δ: 7.67 (d, J=9.4 Hz, 1H), 7.47 (d, J=8.8 Hz, 1H), 7.25 (m, 1H), 6.85 (dd, J=8.5, 2.1 Hz, 1H), 6.55 (d, J=9.4 Hz, 1H), 4.56 (m, 2H), 3.88 (s, 3H), 3.21 (m, 5H), 2.01 (m, 2H).

18.iii. 6-{(R)-5-[(RS)-3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one:

Starting from intermediate 18.ii (100 mg) and the compound of Preparation A (142 mg) and using procedure B, the title intermediate was obtained as a beige solid (41 mg, 21% yield).

MS (ESI, m/z): 537.2 [M+H$^+$].

Example 19

6-{(S)-5-[(RS)-3-hydroxy-3-(7-methoxy-2-oxo-2H-quinolin-1-ylmethyl)pyrrolidin-1-ylmethyl]-2-oxo-oxazolidin-3-yl}-4H-benzo[1,4]thiazin-3-one Starting from intermediate 18.ii (100 mg) and the compound of Preparation F (142 mg) and using procedure B, the title compound was obtained as a beige solid (31 mg, 16% yield).

MS (ESI, m/z): 537.2 [M+H$^+$].

Example 20

6-((S)-5-{2-[(RS)-3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one Starting from intermediate 18.ii (100 mg) and the compound of Preparation G (147 mg) and using procedure B, the

Example 21

6-((R)-5-{2-[(RS)-3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one Starting from intermediate 18.ii (100 mg) and the compound of Preparation C (147 mg) and using procedure B, the title compound was obtained as a beige solid (47 mg, 23% yield).
MS (ESI, m/z): 551.2 [M+H$^+$].

Example 22

4-{1-[(R)-3-(2,3-dihydro-benzo[1,4]dioxin-6-yl)-2-oxo-oxazolidin-5-ylmethyl]-piperidin-4-yl}-6-methoxy-4H-pyrido[2,3-b]pyrazin-3-one Starting from intermediate 15.v (143 mg) and the compound of Preparation B (218 mg) and using procedure B, the title compound was obtained as a beige solid (82 mg, 30% yield).
MS (ESI, m/z): 494.2 [M+H$^+$].

Example 23

6-methoxy-4-(1-{2-[(S)-2-oxo-3-(3-oxo-3,4-dihydro-2H-benzo[1,4]thiazin-6-yl)-oxazolidin-5-yl]-ethyl}-piperidin-4-yl)-4H-pyrido[2,3-b]pyrazin-3-one Starting from intermediate 15.v (130 mg) and the compound of Preparation G (222 mg) and using procedure B, the title compound was obtained as a beige solid (201 mg, 75% yield).
MS (ESI, m/z): 537.2 [M+H$^+$].

Example 24

4-{1-[(R)-3-(3-fluoro-4-methyl-phenyl)-2-oxo-oxazolidin-5-ylmethyl]-piperidin-4-yl}-6-methoxy-4H-pyrido[2,3-b]pyrazin-3-one Starting from intermediate 15.v (143 mg) and the compound of Preparation D (202 mg) and using procedure B, the title compound was obtained as a beige solid (41 mg, 16% yield).
MS (ESI, m/z): 468.2 [M+H$^+$].

Example 25

6-methoxy-4-(1-{2-[(R)-2-oxo-3-(3-oxo-3,4-dihydro-2H-benzo[1,4]thiazin-6-yl)-oxazolidin-5-yl]-ethyl}-piperidin-4-yl)-4H-pyrido[2,3-b]pyrazin-3-one Starting from intermediate 15.v (130 mg) and intermediate C.v (204 mg) and using procedure C, the title compound was obtained as a beige solid (137 mg, 51% yield). MS (ESI, m/z): 537.2 [M+H$^+$].

Pharmacological Properties of the Invention Compounds

In vitro assays
Experimental Methods:
Minimal inhibitory concentrations (MICs; mg/l) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

Results:
All Example compounds were tested against several Gram positive and Gram negative bacteria such as *S. aureus, E. faecalis, S. pneumoniae, M catarrhalis, A. baumanii, E.coli* or *P. aeruginosa*.

Typical antibacterial test results are given in the table hereafter (MIC in mg/l).

| Example No. | MIC for *M. catarrhalis* A894 |
|---|---|
| 1 | ≤0.031 |
| 2 | ≤0.031 |
| 3 | 0.063 |
| 4 | ≤0.031 |
| 5 | ≤0.031 |
| 6 | ≤0.031 |
| 7 | ≤0.031 |
| 8 | 1 |
| 9 | 1 |
| 10 | ≤0.031 |
| 11 | ≤0.031 |
| 12 | 0.5 |
| 13 | ≤0.031 |
| 14 | 0.25 |
| 15 | ≤0.031 |
| 16 | ≤0.031 |
| 17 | ≤0.031 |
| 18 | ≤0.031 |
| 19 | ≤0.031 |
| 20 | ≤0.031 |
| 21 | ≤0.031 |
| 22 | ≤0.031 |
| 23 | ≤0.031 |
| 24 | ≤0.031 |
| 25 | ≤0.031 |

The invention claimed is:
1. A compound of formula I

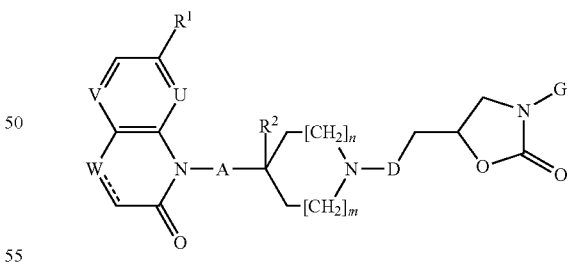

wherein
R$^1$ represents alkoxy or halogen;
U and V each independently represent CH or N;
"-----" is a bond or is absent;
W represents CH or N, or when "-----" is absent, W represents CH$_2$ or NH, with the proviso that U, V and W do not all represent N;
A represents a bond or CH$_2$;
R$^2$ represents H, or provided A is CH$_2$, may also represent OH;
m and n each independently represent 0 or 1;

D represents CH$_2$ or a bond;
G represents a phenyl group substituted once or twice in the meta and/or para position(s) by substituents selected from alkyl, (C$_1$-C$_3$)alkoxy, or halogen, or G is one of the groups G$^1$ and G$^2$

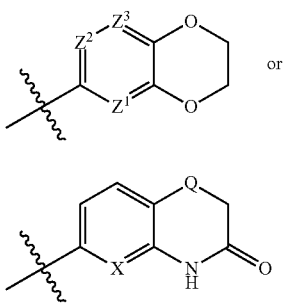

wherein
Z$^1$, Z$^2$, and Z$^3$ each represent CH, or Z$^1$ and Z$^2$ each represent CH, and Z$^3$ represents N, or Z$^1$ represents CH, Z$^2$ represents N, and Z$^3$ represents CH or N, or Z$^1$ represents N, and Z$^2$ and Z$^3$ each represent CH; and X represents N or CH and Q represents O or S; it being understood that if m and n each represent 0, then A represents CH$_2$;
or a salt thereof.

2. The compound according to claim 1, wherein
R$^1$ represents alkoxy;
V represents CH;
U and W each represent CH and "-----" is a bond, or U represents CH, W represents N and "-----" is a bond, or U and W each represent N and "-----" is a bond, or U represents CH, W represents CH$_2$ and "-----" is absent;
A represents a bond or CH$_2$;
R$^2$ represents H, or provided A is CH$_2$, may also represent OH;
m and n each independently represent 0 or 1;
D represents CH$_2$ or a bond;
G represents an phenyl group which is substituted once in a meta and once in the para position by substituents selected from alkyl or halogen, or G is one of the groups G$^1$, and G$^2$,

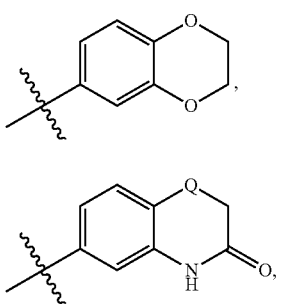

wherein Q represents O or S;
it being understood that if m and n each represent 0, then A represents CH$_2$;
or a salt thereof.

3. The compound according to claim 1, wherein R$^1$ is methoxy; or a salt thereof.
4. The compound according to claim 1, wherein "-----" is a bond; or a salt thereof.
5. The compound according to claim 1, wherein "-----" is absent; or a salt thereof.
6. The compound according to claim 1, wherein A represents a bond; or a salt thereof.
7. The compound according to claim 1, wherein A represents CH$_2$; or a salt thereof.
8. The compound according to claim 7, wherein R$^2$ represents OH; or a salt thereof.
9. The compound according to claim 1, wherein G is a group of the formula

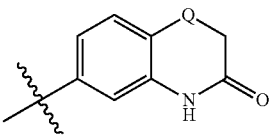

wherein Q represents O or S;
or a salt thereof.
10. The compound according to claim 1, which is:
6-{(R)-5-[3-hydroxy-3-(7-methoxy-2-oxo-2H-quinolin-1-ylmethyl)-azetidin-1-ylmethyl]-2-oxo-oxazolidin-3-yl}-4H-benzo[1,4]thiazin-3-one;
6-{(R)-5-[3-(7-methoxy-2-oxo-2H-quinolin-1-ylmethyl)-azetidin-1-ylmethyl]-2-oxo-oxazolidin-3-yl}-4H-benzo[1,4]thiazin-3-one;
1-{1-[(R)-3-(2,3-dihydro-benzo[1,4]dioxin-6-yl)-2-oxo-oxazolidin-5-ylmethyl]-azetidin-3-ylmethyl}-7-methoxy-1H-quinolin-2-one;
6-{(R)-5-[3-(7-methoxy-2-oxo-2H-quinoxalin-1-ylmethyl)-azetidin-1-ylmethyl]-2-oxo-oxazolidin-3-yl}-4H-benzo[1,4]thiazin-3-one;
6-((R)-5-{2-[3-(7-methoxy-2-oxo-2H-quinolin-1-ylmethyl)-azetidin-1-yl]-ethyl}-2-oxo-oxazolidin-3-yl)-4H-benzo[1,4]thiazin-3-one;
6-((R)-5-{2-[3-(7-methoxy-2-oxo-2H-quinoxalin-1-ylmethyl)-azetidin-1-yl]-ethyl}-2-oxo-oxazolidin-3-yl)-4H-benzo[1,4]thiazin-3-one;
6-{(R)-5-[4-(7-methoxy-2-oxo-2H-quinolin-1-ylmethyl)-piperidin-1-ylmethyl]-2-oxo-oxazolidin-3-yl}-4H-benzo[1,4]thiazin-3-one;
1-{1-[(R)-3-(2,3-dihydro-benzo[1,4]dioxin-6-yl)-2-oxo-oxazolidin-5-ylmethyl]-piperidin-4-ylmethyl}-7-methoxy-1H-quinolin-2-one;
1-{1-[(R)-3-(3-fluoro-4-methyl-phenyl)-2-oxo-oxazolidin-5-ylmethyl]-piperidin-4-ylmethyl}-7-methoxy-1H-quinolin-2-one;
6-{(R)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]thiazin-3-one;
6-{(S)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]thiazin-3-one;
6-{(R)-5-[3-(7-methoxy-2-oxo-3,4-dihydro-2H-quinolin-1-ylmethyl)-azetidin-1-ylmethyl]-2-oxo-oxazolidin-3-yl}-4H-benzo[1,4]oxazin-3-one;
6-{(R)-5-[3-(7-methoxy-2-oxo-2H-quinoxalin-1-ylmethyl)-azetidin-1-ylmethyl]-2-oxo-oxazolidin-3-yl}-4H-benzo[1,4]oxazin-3-one;

1-{1-[(R)-3-(2,3-dihydro-benzo[1,4]dioxin-6-yl)-2-oxo-oxazolidin-5-ylmethyl]-azetidin-3-ylmethyl}-7-methoxy-1H-quinoxalin-2-one;

6-methoxy-4-{1-[(R)-2-oxo-3-(3-oxo-3,4-dihydro-2H-benzo[1,4]thiazin-6-yl)-oxazolidin-5-ylmethyl]-piperidin-4-yl}-4H-pyrido[2,3-b]pyrazin-3-one;

6-methoxy-4-{1-[(R)-2-oxo-3-(3-oxo-3,4-dihydro-2H-benzo[1,4]oxazin-6-yl)-oxazolidin-5-ylmethyl]-piperidin-4-yl}-4H-pyrido[2,3-b]pyrazin-3-one;

6-{(R)-5-[(R)-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;

6-{(R)-5-[3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;

6-{(S)-5-[3-hydroxy-3-(7-methoxy-2-oxo-2H-quinolin-1-ylmethyl)-pyrrolidin-1-ylmethyl]-2-oxo-oxazolidin-3-yl}-4H-benzo[1,4]thiazin-3-one;

6-((S)-5-{2-[3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one;

6-((R)-5-{2-[3-hydroxy-3-(7-methoxy-2-oxo-2H-quinolin-1-ylmethyl)-pyrrolidin-1-yl]-ethyl}-2-oxo-oxazolidin-3-yl)-4H-benzo[1,4]thiazin-3-one;

4-{1-[(R)-3-(2,3-dihydro-benzo[1,4]dioxin-6-yl)-2-oxo-oxazolidin-5-ylmethyl]-piperidin-4-yl}-6-methoxy-4H-pyrido[2,3-b]pyrazin-3-one;

6-methoxy-4-(1-{2-[(S)-2-oxo-3-(3-oxo-3,4-dihydro-2H-benzo[1,4]thiazin-6-yl)-oxazolidin-5-yl]-ethyl}-piperidin-4-yl)-4H-pyrido[2,3-b]pyrazin-3-one;

4-{1-[(R)-3-(3-fluoro-4-methyl-phenyl)-2-oxo-oxazolidin-5-ylmethyl]-piperidin-4-yl}-6-methoxy-4H-pyrido[2,3-b]pyrazin-3-one; or 6-methoxy-4-(1-{2-[(R)-2-oxo-3-(3-oxo-3,4-dihydro-2H-benzo[1,4]thiazin-6-yl)-oxazolidin-5-yl]-ethyl}-piperidin-4-yl)-4H-pyrido[2,3-b]pyrazin-3-one;

or a salt thereof.

11. A medicament comprising; a compound according to claim 1, or a pharmaceutically acceptable salt thereof.

12. A pharmaceutical composition comprising a therapeutically effective amount of a compound according to claim 1, or a pharmaceutically acceptable salt thereof, and at least one therapeutically inert excipient.

13. A method of treating a bacterial infection in a patient comprising administering to the patient in need thereof, a therapeutically effective amount of the compound according to claim 11.

14. A method of treating a bacterial infection in a patient comprising administering to the patient in need thereof, a therapeutically effective amount of the composition according to claim 12.

15. The compound according to claim 1, wherein A represents a bond and m and n each represent 1; or a salt thereof.

16. The compound according to claim 1, wherein A represents $CH_2$ and one of m and n represents 0 and the other represents 1; or a salt thereof.

17. The compound according to claim 1, wherein A represents $CH_2$ and m and n each represent 1; or a salt thereof.

* * * * *